United States Patent
Eason et al.

(10) Patent No.: US 7,845,349 B2
(45) Date of Patent: Dec. 7, 2010

(54) INHALER

(75) Inventors: Stephen William Eason, Norfolk (GB); Michael Edgar Newton, Norfolk (GB); Roger William Clarke, Cambridge (GB); Matthew Neil Sarkar, Cambridge (GB)

(73) Assignee: Vectura Limited, Chippenham, Wilts (GB)

( * ) Notice: Subject to any disclaimer, the term of this patent is extended or adjusted under 35 U.S.C. 154(b) by 1045 days.

(21) Appl. No.: 10/594,730

(22) PCT Filed: Mar. 30, 2005

(86) PCT No.: PCT/GB2005/050044

§ 371 (c)(1),
(2), (4) Date: Oct. 30, 2006

(87) PCT Pub. No.: WO2005/094924

PCT Pub. Date: Oct. 13, 2005

(65) Prior Publication Data

US 2008/0264415 A1    Oct. 30, 2008

(30) Foreign Application Priority Data

Apr. 2, 2004  (GB) ................................ 0407627.9

(51) Int. Cl.
*A61M 16/00* (2006.01)
(52) U.S. Cl. .............................. 128/203.15; 128/203.12
(58) Field of Classification Search ............ 128/203.15, 128/203.12, 203.23, 203.24; 604/87, 208, 604/218, 220, 224, 225
See application file for complete search history.

(56) References Cited

U.S. PATENT DOCUMENTS

| 5,046,493 | A  |   | 9/1991  | Kropkowski et al. ... 128/203.15 |
| 5,301,666 | A  | * | 4/1994  | Lerk et al. ............. 128/203.15 |
| 5,349,947 | A  | * | 9/1994  | Newhouse et al. ...... 128/203.21 |
| 5,582,598 | A  | * | 12/1996 | Chanoch ..................... 604/208 |
| 5,740,794 | A  |   | 4/1998  | Smith et al. ............. 128/203.15 |
| 5,816,504 | A  |   | 10/1998 | Zuckschwerdt et al. ..... 239/373 |
| 6,029,661 | A  |   | 2/2000  | Whaley et al. ......... 128/203.15 |
| 6,302,101 | B1 |   | 10/2001 | Py ........................ 128/200.22 |
| 6,679,256 | B2 | * | 1/2004  | Ingle et al. ............. 128/203.21 |
| 2004/0056049 | A1 | | 3/2004 | Stradella .................. 222/321.7 |

FOREIGN PATENT DOCUMENTS

| DE | 4227899 | 2/1994 |
| EP | 1186350 | 3/2002 |
| GB | 2316451 | 2/1998 |
| WO | 9211049 | 7/1992 |

* cited by examiner

*Primary Examiner*—Justine R Yu
*Assistant Examiner*—Christopher Blizzard
(74) *Attorney, Agent, or Firm*—Davidson, Davidson & Kappel, LLC

(57) ABSTRACT

An inhaler (1) for the delivery of a dose of powdered medicament for inhalation by a user comprising a housing (2) containing a cylinder (5) defining a chamber (5a) and a piston (6) movably received in the cylinder to enable a user to generate a charge of compressed air in the chamber to entrain a dose when the charge is released, wherein the cylinder and the piston include co-operating means (8, 9) thereon operable to draw the piston into the cylinder to compress a charge of air in the chamber in response to rotation of the piston.

29 Claims, 15 Drawing Sheets

INHALER

This application is a national phase of International Application No. PCT/GB2005/050044, filed Mar. 30, 2005, which claims priority to GB 0407627.9, filed Apr. 2, 2004.

FIELD OF THE INVENTION

The present invention relates to an inhaler for the delivery of medicament in powdered form to the lung.

BACKGROUND OF THE INVENTION

Traditionally, inhalers have been used to deliver medicament to the lung to treat local diseases of the lung such as asthma. However, when the inhaled particles are in the range 1 to 3 microns they can reach the deep lung (alveoli) and cross into the bloodstream. This systemic delivery of pharmaceutically-active agents to the bloodstream via the lungs using an inhalation device has become a particularly attractive form of administering drugs to a patient many of whom are reluctant to receive drugs via injection using a needle. Furthermore, the administration of a drug using an inhaler may be carried out discreetly and in public without any of the known difficulties associated with needle injections.

SUMMARY OF THE INVENTION

An inhaler for a delivery of a dose of a powdered medicament for inhalation by a user comprising a housing containing a cylinder and a piston together defining a chamber, the piston being movable relative to the cylinder.

It will be appreciated that it is important to ensure that the powdered medicament is delivered within an accurately controlled range of particle size so that the particles will reach the lung and be absorbed into the bloodstream. Typically, when an active dry powder inhaler is used, the particles are entrained in a charge of gas or air which carries the particles out of the inhaler and into the patient's airway. The airflow also assists in the de-agglomeration and aerosolisation of the particles and helps to prevent deposition of the particles within the device. These aspects are very important when a large repeatable dose of fine particles is required.

An active dry powder inhaler may use a charge of compressed gas or air to aerosolise a dose of medicament for inhalation by a user. A pre-metered dose of medicament is often contained in individual blisters and the inhaler generally includes means for accessing the dose contained in a blister, such as a piercing element, which is operable when the user is ready to inhale the dose. The inhaler also includes a valve assembly, which may or may not be breath actuated, operable to supply a charge of compressed air from a source through the pierced blister to entrain the dose contained therein and aerosolise it so that it passes into the user's mouth via a mouthpiece and down into their lungs.

The present invention is concerned with an inhaler in which a user manually generates a charge of compressed air in a cylinder within the device each time it is used so that the charge can subsequently be released to aerosolise and entrain a dose of dry powder drug. Although inhalers incorporating a pump to enable the user to manually generate a charge of compressed air for aerosolisation of a dose of medicament are known from, for example, U.S. Pat. Nos. 5,740,794 and 5,785,049, the devices known from these documents have a complicated lever mechanism connected to the pump via a series of linkages to increase the user's mechanical advantage. In addition to having a complicated construction and consisting of many separate components, the lever mechanism and linkages take up a considerable amount of space and so increase the overall size of the device.

It is also known to provide a manually operated pump for example a bicycle pump for generating a charge of compressed air in which the pump works to compress the air in both directions of its stroke. However, this type of pump also has a complicated construction.

Another method for manually generating a charge of compressed air for use in aerosolising a dose of medicament in an inhaler is to pump up an accumulator via a non-return valve. In accordance with this method, gas or air in a pump chamber is compressed and forced through a non-return (one way) valve into an accumulator chamber. This action is repeated until the required pressure in the accumulator is achieved. A disadvantage with this type of manual pump is that further actions of the pump continue to accumulate pressure and so a higher pressure than actually required is generated in the accumulator chamber leading to increased risk of a leak or blow out from the accumulator chamber. Although this problem can be addressed by providing the inhaler with a pressure sensor and interlock or by a relief valve, these components introduce further complexity into the device, which is undesirable. Furthermore, in this arrangement, the pump must overcome the (small) pressure drop across the non-return valve meaning that the pump needs to generate a higher pressure.

A well-known problem with manually operated piston pumps is that the amount of force required to compress the air increases as the piston slides further into its cylinder as the air is compressed. During the early part of the stroke the force is low and the piston feels relatively easy to slide into the cylinder but, during the later part of the stroke, the force increases significantly and the piston becomes much harder to move. This is illustrated in FIG. 1 from which it can be seen that in a pump having a cylinder diameter of 28 mm, an open volume of 37.5 ml and a compressed volume of 15 ml at 1.5 bar, the force that must be applied to the piston throughout the compression stroke steadily increases. This means that the effort that a user must exert in order to fully prime the pump with a charge of compressed air ready for use is high, especially for a user who is of older age or of limited mobility. As a result, this type of inhaler is not widely used despite having the advantage that a separate pre-pressurised source of air or gas is no longer required.

Although the aforementioned problem is the main reason why a manual piston pump is not often used, there are a number of other factors that must also be taken into account in addition to the increasing force that must be applied to the piston during the compression stroke, and these are now referred to in more detail below:

The maximum force or torque that can be applied by a user. The pressure generated by a user is determined by the maximum force applied by the user and the area of the piston (pressure=force applied/area of piston pump). Anthropometric data gives forces and torques that can reasonably be expected to be achieved by a notional population of users as a guideline for designing products. For example, the mean twisting torque that can be applied to a 40 mm diameter screw top by a healthy female aged 62-92 years is 1.58 Nm (Rohles et al (1983) Proceedings of the Human Factors Society $27^{th}$ Annual Meeting).

The maximum acceptable distance over which the force can be applied. In a simple piston pump, the volume of the compressed gas and the pressure is controlled by the extension of the piston and the final gas volume.

The maximum acceptable size of the inhaler device in which the charge of gas must be generated. This is related directly to the volume of compressed gas and the volume of the pump in the extended, unpressurised case.

These relationships between pressure, volume and force place considerable constraints on the design of a pump especially when it is desirable to have a compact, simple inhaler device and a pump that does not require a large operating force.

It will also be appreciated that it is very important that an inhaler is used correctly so that a full dose of medicament is delivered to the user each time the device is used. It is therefore desirable to incorporate a system into the device that prevents its misuse by, for example, failing to generate a full charge of compressed air before releasing the charge to aerosolise a dose. However, at the same time the sequence of steps that must be performed to enable the device to be operated must be obvious and intuitive to the user so that it encourages the user to operate the inhaler in the correct sequence.

It is an object of the present invention to overcome or substantially alleviate the problems with conventional inhalation devices of the type discussed above.

According to the invention, there is provided an inhaler for the delivery of a dose of powdered medicament for inhalation by a user comprising a housing containing a cylinder and a piston together defining a chamber, the piston and cylinder being slideable relative to each other during a compression stroke in response to the application of a load thereto by the user to generate a charge of compressed air in the chamber for entraining a dose when the charge is released, the inhaler including means for increasing the mechanical advantage during a compression stroke so that the effort applied by the user remains substantially constant throughout the compression stroke irrespective of the increase in pressure in the chamber.

As the effort required by the user to prime the pump is kept relatively constant throughout the compression stroke, by a simple and uncomplicated mechanism which provides the user with a mechanical advantage, the pump is much easier for the user to prime despite the increase in pressure in the chamber during the compression stroke.

According to another aspect of the invention there is provided an inhaler for the delivery of a dose of powdered medicament for inhalation by a user comprising a housing containing a cylinder and a piston together defining a chamber, piston being movable relative to the cylinder to enable a user to generate a charge of compressed air in the chamber to entrain a dose when the charge is released, wherein the cylinder and the piston include means thereon operable to compress a charge of air in the chamber in response to rotation of the piston relative to the cylinder.

In a preferred embodiment of the invention, the co-operating means comprises a cam track and a pin located in the cam track so as to slide freely therein during rotation of the piston.

The cam track is preferably formed in the piston and the pin is mounted so as to extend radially from the cylinder and locate in the cam track.

Advantageously, at least a portion of the cam track follows a helical path that extends along the axis around the outside of the piston.

In a preferred embodiment, the ends of the helical portion of the cam track are joined by a second straight portion of cam track extending parallel to the axis of the cylinder so that the cam track forms a complete circuit for the pin during movement of the piston into and out of the cylinder.

Conveniently, the helical portion of the cam track extends substantially 360 degrees around the piston.

The cam track preferably includes a region between the helical portion and the straight portion having a pitch that is substantially zero degrees relative to a plane perpendicular to the axis of the cylinder.

The helical portion of the cam track may include another region intermediate its ends having a pitch that is substantially zero degrees relative to a plane perpendicular to the axis of the cylinder.

In one embodiment, the cam track includes a detent therein configured so that the pin and the detent co-operate with each other during rotation of the piston so that additional torque must be applied to the piston by the user to force the pin past the detent.

Advantageously, the pin is forced into engagement with the detent by the pressure in the reservoir such that the additional torque required to pass the detent is high when the reservoir is charged and low when the reservoir is not charged.

The inhaler according to one embodiment of the invention includes an interlock mechanism to prevent rotation of the piston out of said home position prior to disengagement of the interlock mechanism.

The interlock mechanism conveniently comprises a slide member on the housing movable into and out of engagement with the piston when the piston is in its home position.

The inhaler may include a mouthpiece and a cap pivotable between an open position for inhalation through the mouthpiece and a closed position in which the mouthpiece is covered by the cap. In this instance, movement of the slider may be prevented by the cap when the cap is in its closed position.

In one embodiment, the helical portion of the cam-track has a constant pitch angle. However, in a particularly advantageous embodiment, the helical portion of the cam track has a pitch angle that varies along the length of the piston.

When the helical portion of the cam track has a variable pitch angle, the pitch angle of the cam track may vary so that it provides a greater linear compression per angle of rotation during initial rotation of the piston into the cylinder and, a lower rate of compression per angle of rotation during later rotation of the piston into the cylinder.

Ideally, the pitch angle of the cam track is configured so that the torque applied by the user throughout rotation of the piston into the cylinder to compress a charge of air remains substantially constant.

To simplify manufacture of the piston, it may be advantageously formed in two parts such as a body portion and a handle portion. The cam track can then be formed at the interface between the body portion and the handle portion.

The body portion of the piston may comprise a stem part and a head part of larger diameter than the stem part, a part helically shaped shoulder being formed at the interface between the head part and the stem part. Similarly, the handle portion may comprise a cylindrical body to receive the stem part of the body portion, the end face of the handle portion in which the stem part is received being part helical in shape to correspond to the part helically shaped shoulder of the body portion.

In another embodiment, the inhaler preferably includes a valve module including a valve body and a rotary valve plate rotatably mounted on the body, the piston and the rotary valve plate including co-operating means that engage as the piston is rotated into the cylinder so that the rotary valve plate rotates together with the piston relative to the valve body.

Preferably, the valve body includes a main diaphragm valve port and a pilot reservoir port, the rotary valve plate being configured to open and close said ports as the rotary valve plate rotates.

The rotary valve plate preferably has first and second apertures therein that align with the main diaphragm valve port and the pilot reservoir port respectively, as the rotary valve plate rotates, to open said ports.

In one embodiment, the apertures in the rotary valve plate are configured such that the pilot reservoir port is opened prior to opening of the main diaphragm port and so that the apertures in the rotary valve plate are configured such that the pilot reservoir port is closed prior to closing of the main diaphragm port. This means that the reservoir cannot be discharged until it is at substantially the correct pressure.

Ideally, the co-operating means engage for approximately the last 180 degrees of rotation of the piston into the cylinder so that the rotary valve plate rotates relative to the valve module through 180 degrees.

The invention also provides a method of operating an inhaler for the delivery of a dose of powdered medicament for inhalation by a user comprising a housing containing a cylinder defining a chamber and a piston movably received in the cylinder, the method including the step of withdrawing the piston from the cylinder and rotating the piston to draw it back into the cylinder to generate a charge of compressed air in the chamber.

The method preferably includes the step of withdrawing the piston from the cylinder by applying an axial force thereto.

Preferably the method also includes the step of opening the cap and moving the slider to disengage the piston before withdrawing the piston from the cylinder. Embodiments of the invention will now be described, by way of example only, with reference to FIGS. 2 to 13 of the accompanying drawings, in which:—

Figure 10:
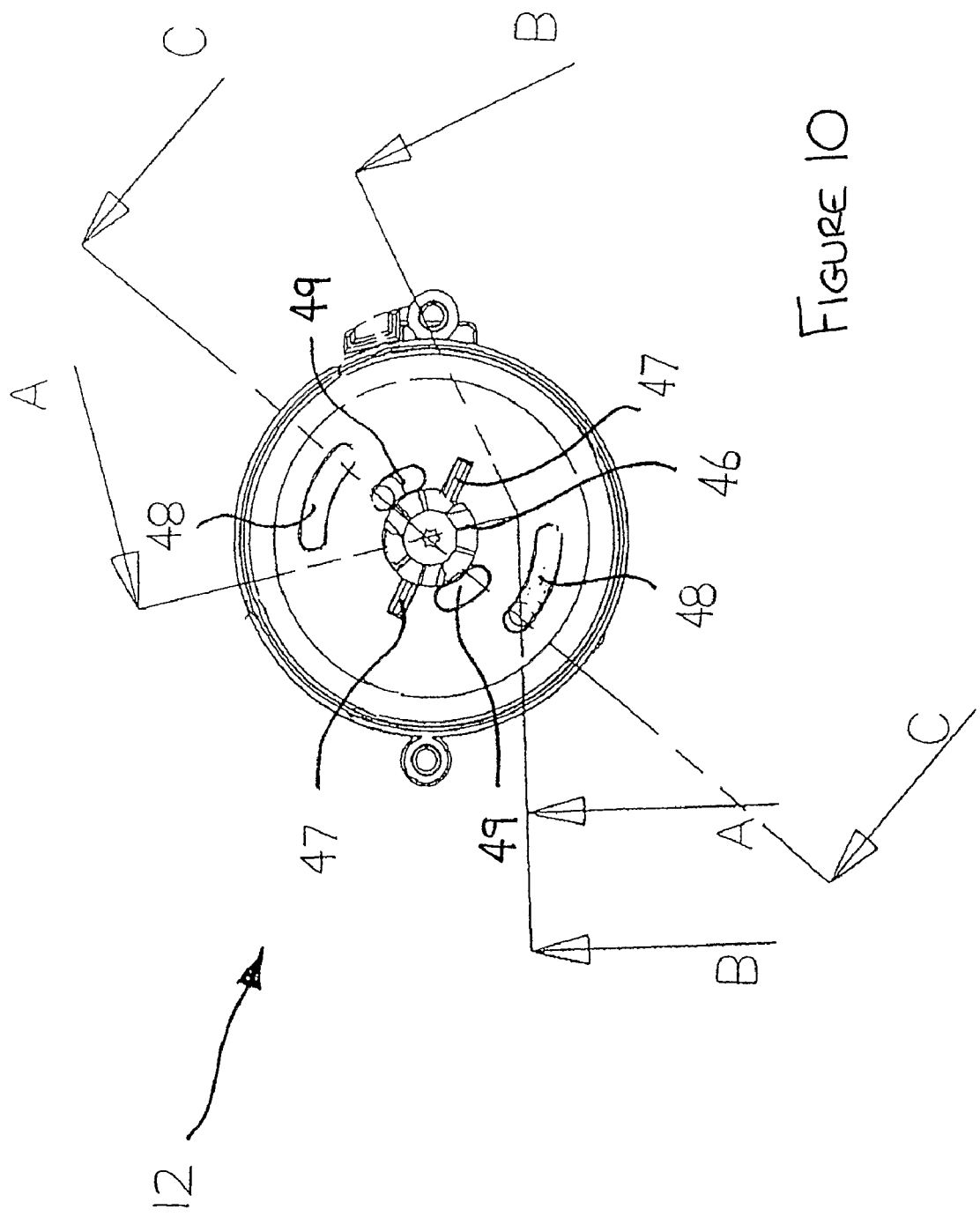
FIG. 10 is a bottom plan view of the valve assembly.
Figure 11:
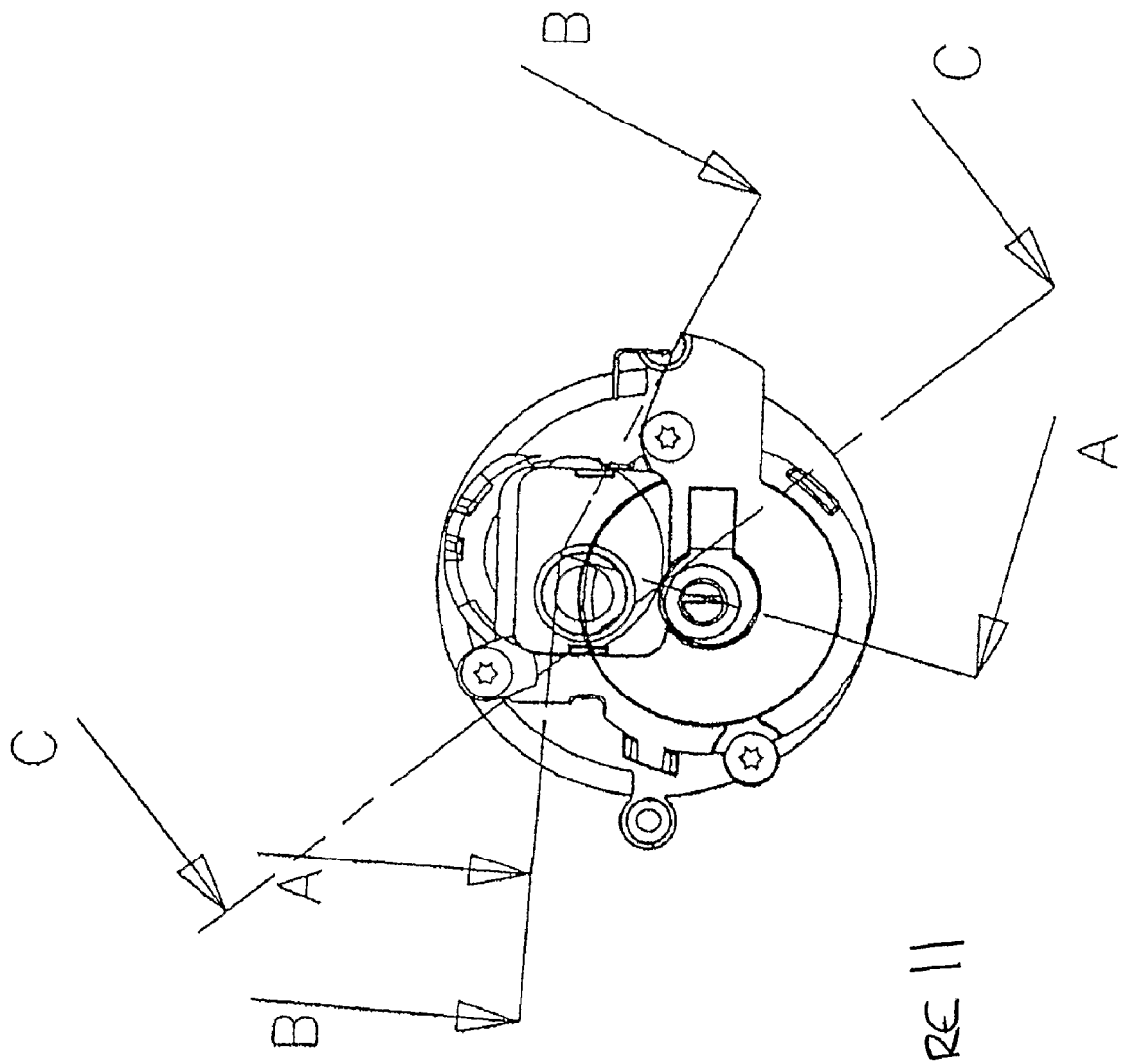
FIG. 11 is a top plan view of the valve assembly shown in FIG. 10.
Figure 12:
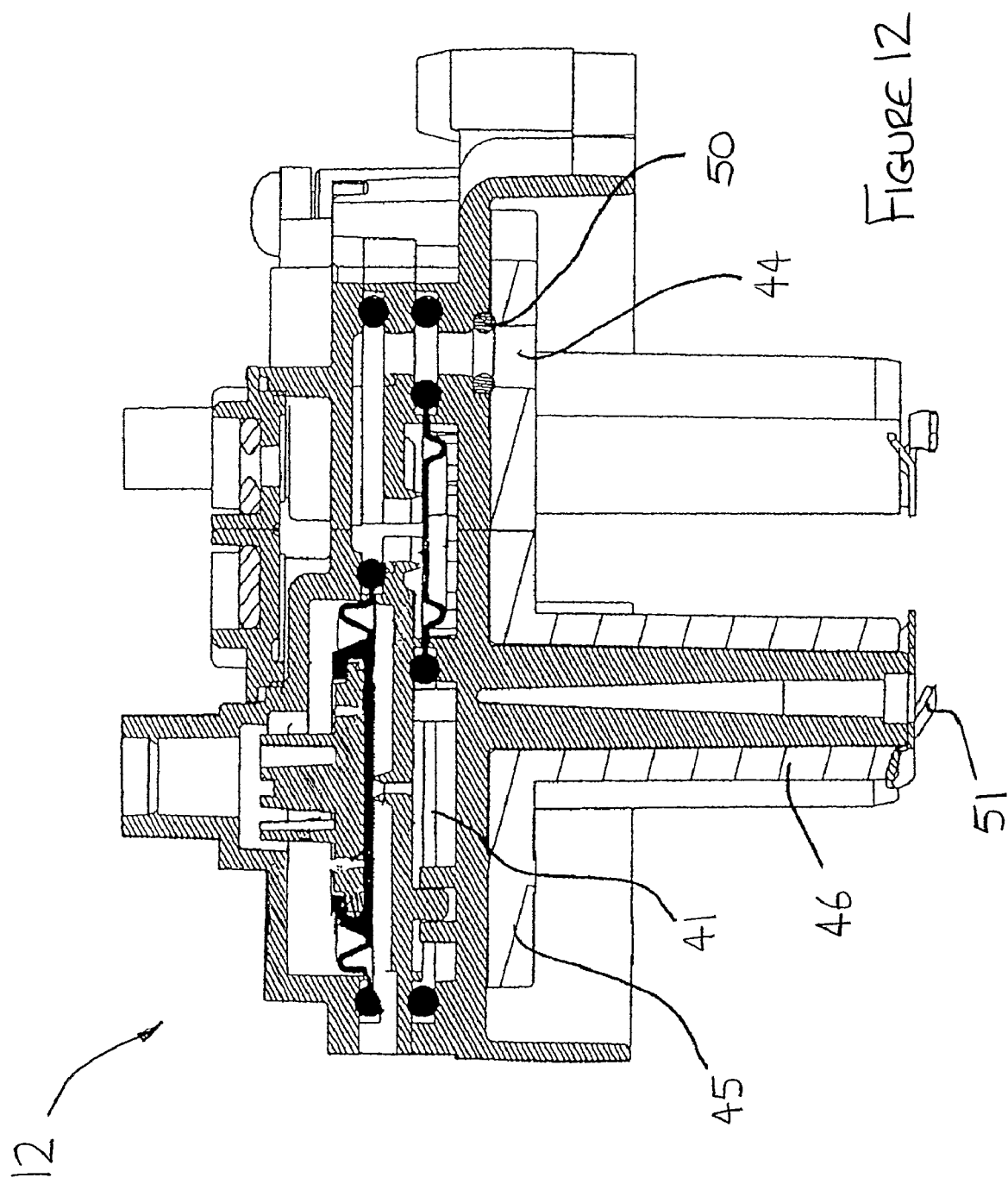
Figure 13:
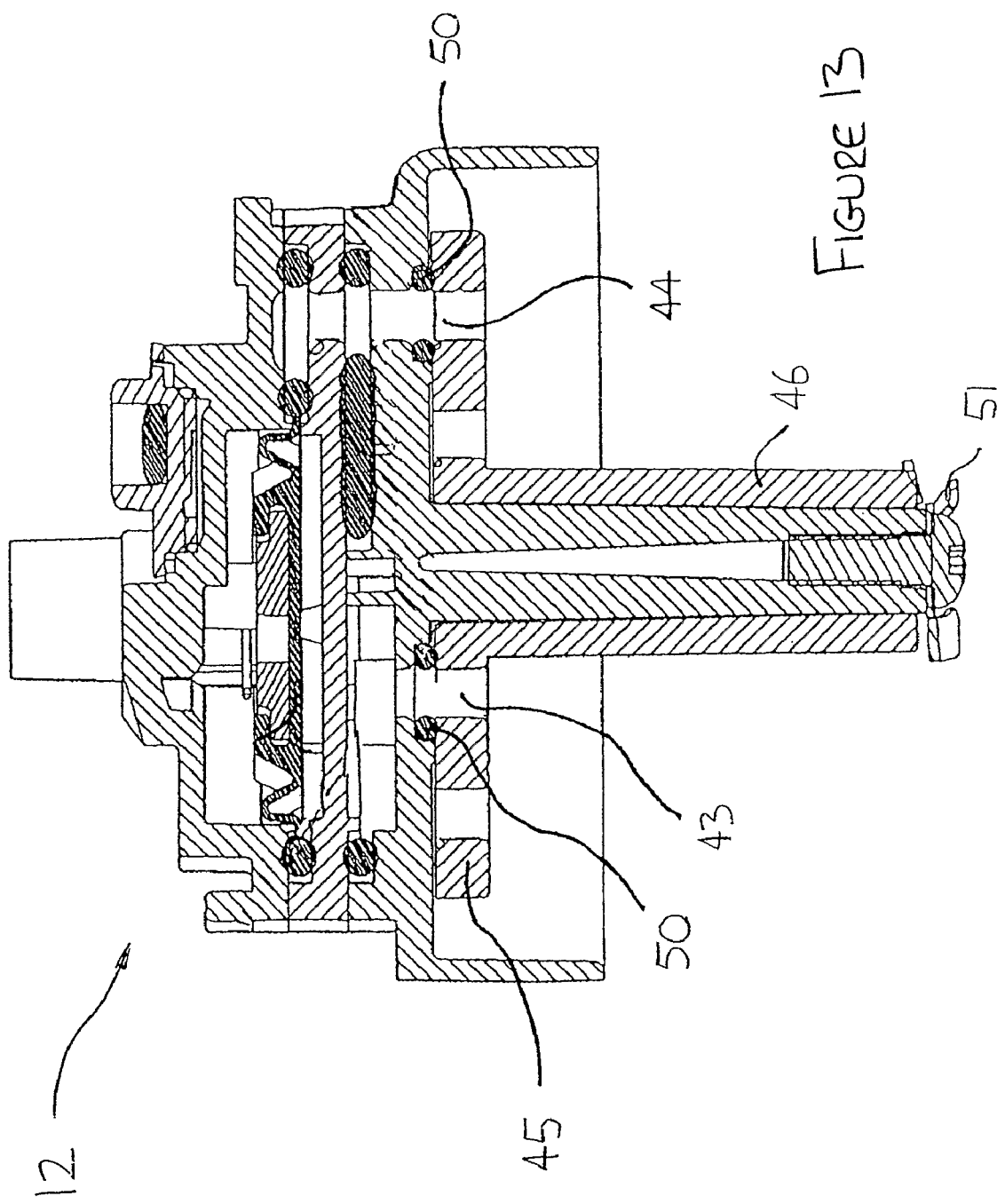

FIG. 12 side sectional view of the valve assembly taken along line A-A in FIG. 10; and FIG. 13 is a side sectional view of the valve assembly taken along line C-C in FIG. 10.

DETAILED DESCRIPTION OF THE INVENTION

Figure 2:
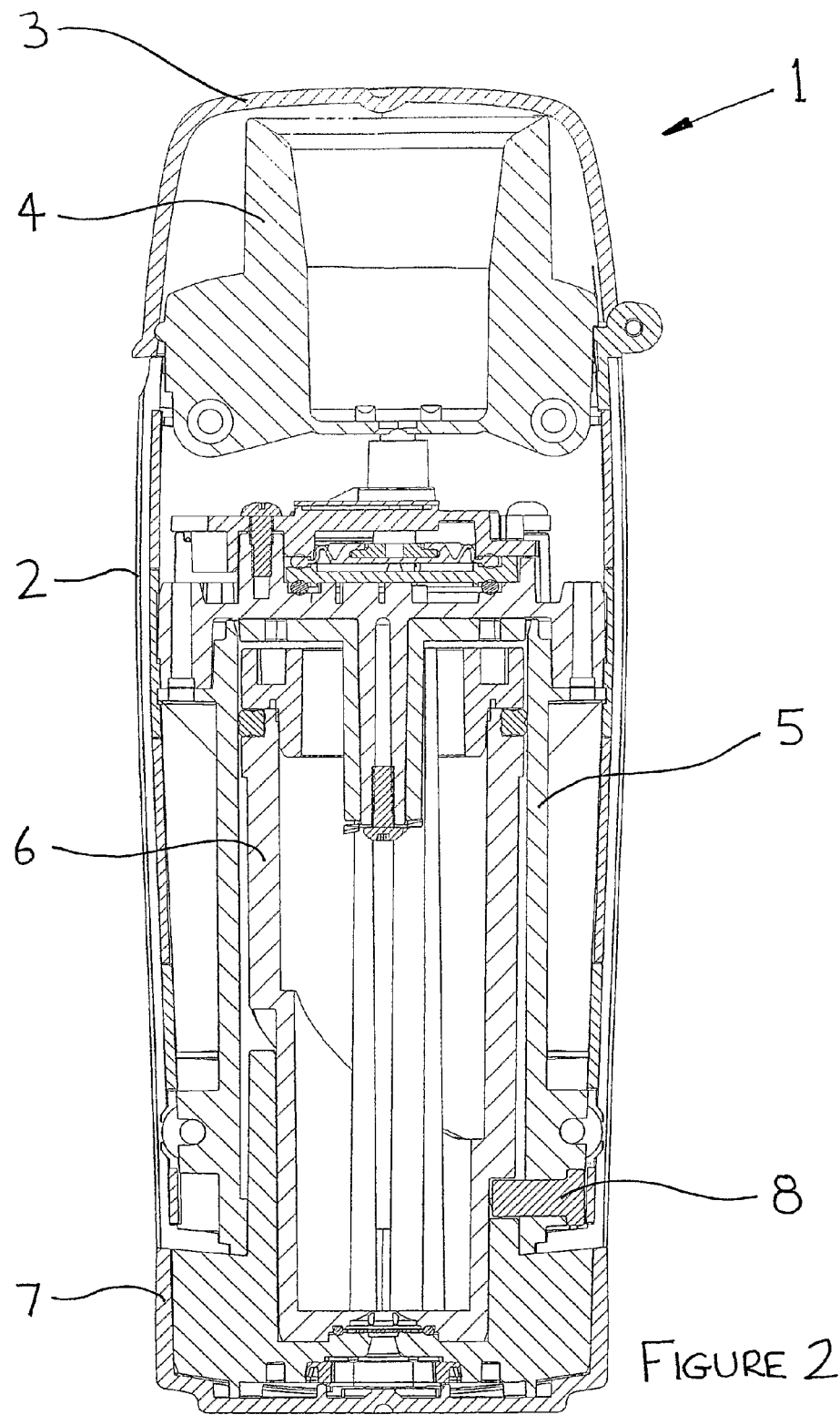
FIG. 2 is a longitudinal cross-sectional view of an inhaler according to the present invention with the piston in its fully "home" position and the mouthpiece cap closed.
Figure 3:
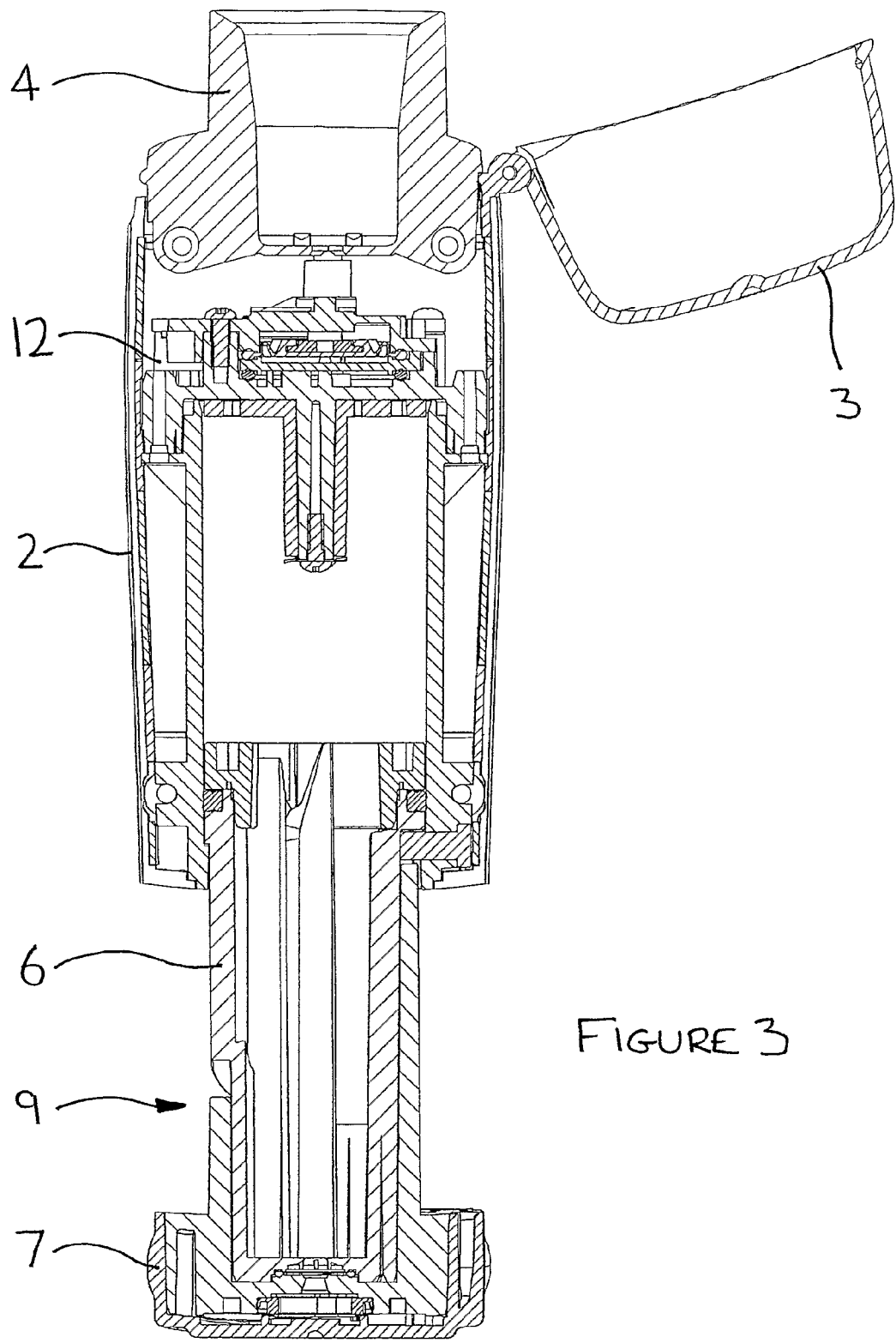
FIG. 3 is the longitudinal cross-sectional view of FIG. 2, in which the piston has been withdrawn from its cylinder into its extended position and the mouthpiece cap opened.

Referring now to the drawings, there is shown in FIG. 2 an inhaler 1 according to an embodiment of the invention comprising a housing 2 having a cap 3 pivotally attached thereto and which covers a mouthpiece 4 through which a user can inhale a dose of medicament from the device 1 once the cap 3 has been rotated with respect to the housing into the position shown in FIG. 3.

The interior of the housing 2 contains a cylinder 5 defining a chamber 5a therein (see FIG. 3). A pump or piston 6 in the form of a tube open at one end is received in the cylinder 5 and is movable between a first "home" or retracted position in which the piston 6 is fully received within the cylinder 5, as shown in FIG. 2 and FIGS. 8A to 8C, and a fully extended position in which the piston protrudes out of the cylinder 5 from the end of the housing 2, as shown in FIG. 3 and FIG. 8E. Movement of the piston 6 between the home and extended positions is achieved through manipulation of a handle 7 forming part of the piston 6. The handle 7 and/or the housing 2 may be of a similar size and shape so that the handle 7 forms an extension to the housing 2 when the piston 6 is in the home position so that the handle 7 lies flush with the outer surface of the housing 2. However, at least one of the handle 7 and/or the housing 2 does not have a circular cross-section so that when the piston 6 is rotated relative to the housing 2, the housing 2 and handle 7 are no longer flush with each other and the handle 7 protrudes radially outwardly further than the housing 2. For example, the housing 2 and/or the handle 7 may have an oval shape in cross-section. This enables a user to visually determine the position of the piston 6 within the housing 2.

As the piston 6 moves from its extended back to its home position, the volume of air in the chamber 5a inside the cylinder 5 is reduced so that the full volume of air originally contained in both the chamber 5a and the piston 6 is reduced and the air compressed. As a result of this compression of the air within the chamber 5a, its pressure increases. It will be appreciated that in this arrangement, repeated priming of the pump, i.e. by pumping the piston 6 in and out of the cylinder 5, does not result in a continuous increase in pressure because the same quantity of gas is repeatedly being compressed and uncompressed in the chamber 5a as the piston 6 moves in and out of the cylinder 5. Therefore, the required pressure will always be obtained and can never be exceeded on successive operations of the pump, unlike in a pump incorporating an accumulator.

Movement of the piston 6 from its extended position shown in FIG. 3 to its home position shown in FIG. 2 will now be described. The piston 6 is prevented from sliding directly into the cylinder 5 from its extended position as a result of the application of an inwardly directed force thereto along the longitudinal axis of the piston 6 because a pin 8 is attached to the cylinder 5 and protrudes radially into the chamber 5a. A cam groove or track 9 is formed on the outer surface of the piston 6, a part 9a of which is helical in shape and extends around the outside of the piston 6. Due to the helical form of part 9a of the cam groove 9, the piston 6 will only move into the cylinder 5 in response to the application of torque to the piston 6 by the user via the handle 7. As the piston 6 is rotated, the pin 8 travels along the helical part 9a of the cam groove 9 so that the piston 6 is effectively screwed into the cylinder 5 thereby compressing the air in the chamber 5a and priming the pump.

To prevent the piston 6 from unscrewing from the cylinder 5 when it is released due to the pressure generated in the chamber 5a, the inhaler 1 is provided with a mechanism (not shown) to prevent rotation or movement of the piston 6 in the opposite direction, such as a ratchet having co-operating members on the piston 6 and cylinder 5. This non-return mechanism operates when the piston is in the home position and in the primed position ready for inhalation.

Although, in one embodiment, the helical part 9a of the cam groove 9 may have a constant pitch angle, in a particularly advantageous embodiment of the invention, the pitch angle of the helical part 9a is modified along the length of the piston 6 so that the applied torque remains substantially constant throughout the compression stroke. This is achieved by varying the pitch angle of the helical part 9a to provide a greater linear compression per angle of rotation in the early part of the stroke where the force required to compress the gas is low and, a lower rate of compression per angle of rotation in the later part of the stroke where the force required to compress the gas is higher. This non-linear relationship of compression relative to the angle of rotation of the piston 6 is beneficial in a manually operated inhaler 1 of this type in which the available torque is limited by the strength of the user.

The torque, T required at any given point in the compression stroke can be stated mathematically as:

$$T = \frac{Fp(\sin\theta + \mu\cos\theta)d}{(\cos\theta - \mu\sin\theta)s}$$

Figure 1:
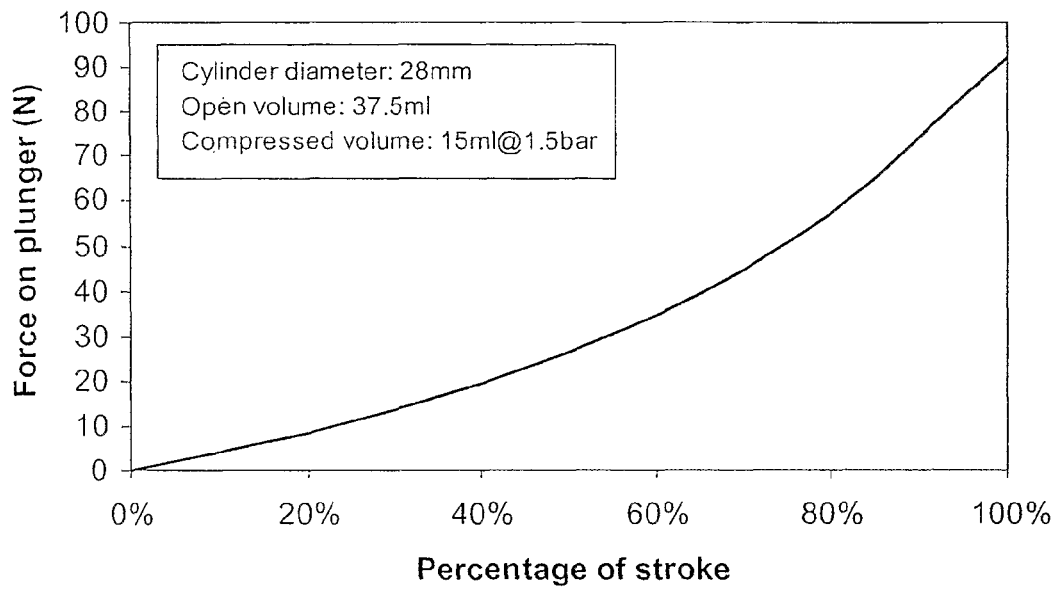
FIG. 1 illustrates a graph to show the relationship between the force applied to a piston and the percentage of stroke through which the piston has moved during compression.
Figure 4:
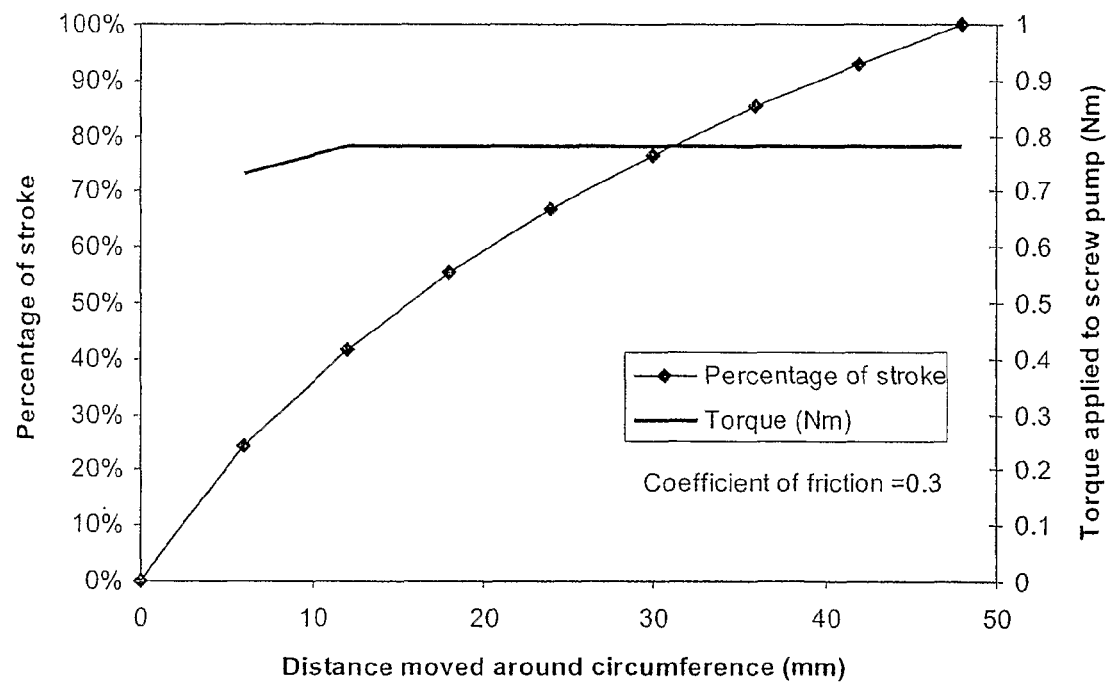
FIG. 4 is a graph to illustrate how a variable pitch screw pump translates the required pump force into an approximately constant torque to be applied by the user.

Where
$F_p$=pressure force from the compressed gas
d=piston diameter
θ=screw pitch angle
μ=coefficient of friction between the sliding parts of the thread From this equation, it will be apparent that it is possible to maintain the torque, T at an approximately constant level by varying the pitch angle θ to compensate for the change in $F_p$ as the gas is compressed. This is shown diagrammatically in the graph of FIG. 4 which illustrates how a piston having a cam groove with a variable pitch translates the required pump force into an approximately constant torque to be applied by the user.

By way of example, and using a piston 6 having a diameter of 28 mm and a stroke of 37 mm which compresses a charge of gas with a volume of 37.5 ml at atmospheric pressure to 15 ml and a gauge pressure of 1.5 bar, and by assuming a coefficient of friction between the moving parts of 0.3 and final pitch angle θ at maximum compression of 24 degrees, the maximum torque required to rotate the piston 6 is 0.78 Nm and it turns through 0.76 of a revolution (275 degrees) to complete the compression of the gas.

A piston having a constant pitch cam groove of the same diameter requiring the same maximum torque would need to be turned through 1.32 revolutions (476 degrees) to complete the compression. (Number of revolutions=stroke/(pi*d*tan θ) where stroke=37 mm, pitch angle θ=24 degrees and screw diameter d=20 mm). Therefore, although a piston having a cam groove with a constant pitch is easier for a user to operate than a conventional sliding piston, a constant pitch pump "wastes" over 40% of the energy available in compressing the charge of gas compared with a piston having a cam groove with a variable pitch. Consequently, it will be appreciated that a piston having a cam groove with a variable pitch is more efficient at generating the same charge of compressed gas and so represents a more preferable embodiment of the invention.

Figure 5:
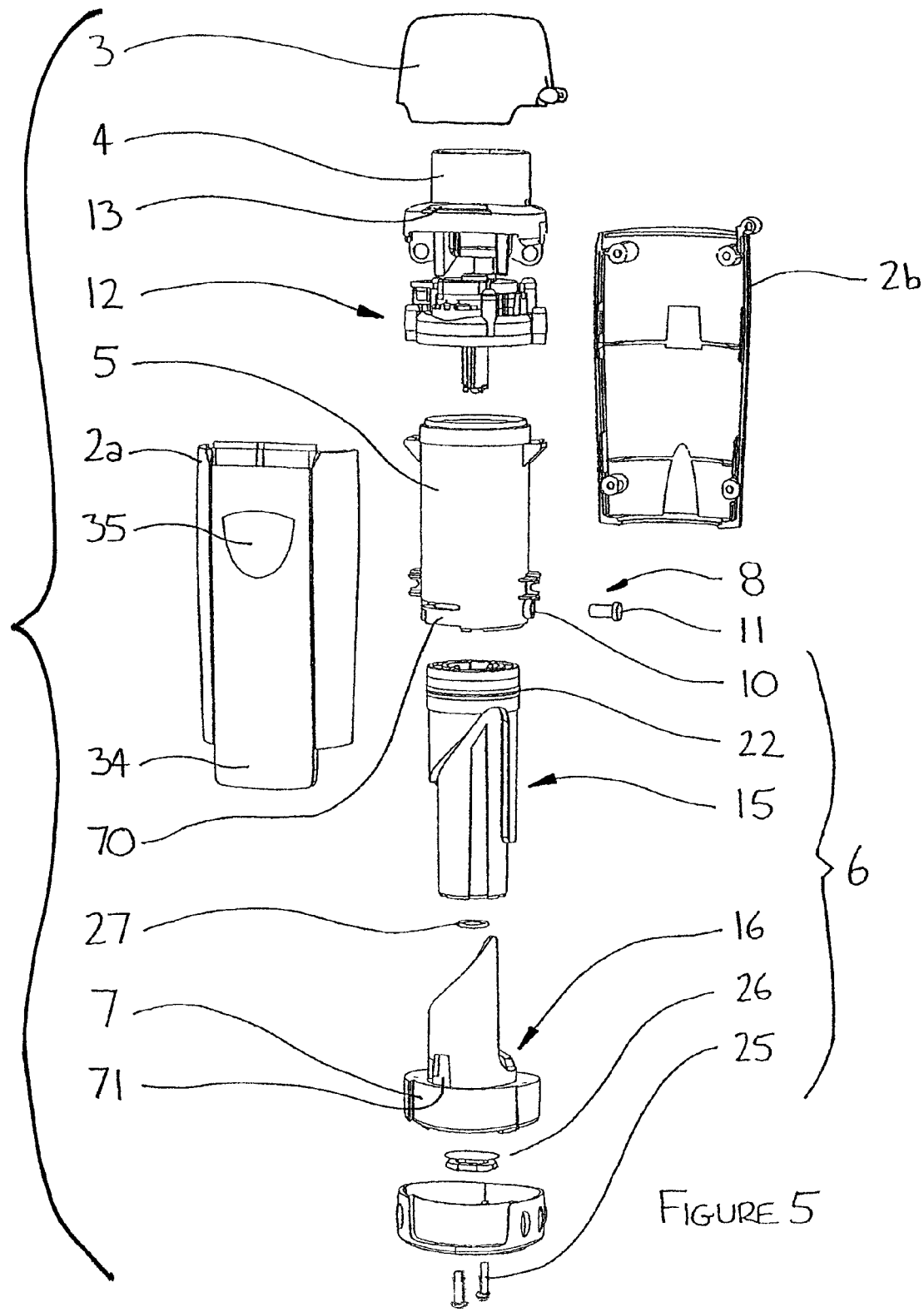
FIG. 5 is an exploded perspective view of the inhaler shown in FIGS. 2 and 3.

An exploded perspective view of an embodiment of the inhaler illustrated in FIGS. 2 and 3 is shown in FIG. 5 from which it can be seen that the housing 2 comprises two semi-cylindrical parts 2a,2b that are joined along their length with the cylinder 5 mounted between them. An aperture 10 is provided in the cylinder 5 adjacent to its lowermost edge in which the pin 8 locates with a shank portion extending radially into the chamber 5a. The pin 8 has a head 11 that is larger than the aperture 10 in which the shank of the pin 8 fits to locate the pin 8 in the sidewall of the cylinder 5. However, in a particularly preferred embodiment, the pin is an integral part of the cylinder 5 to reduce the number of components. A valve module 12 is mounted on and closes the open upper end of the cylinder 5 and has a path therethrough for the supply of a charge of compressed gas from the cylinder 5 through a blister (not shown) that may be inserted into the valve assembly 12 through an aperture or slot 13 in the side of the housing 2.

Figure 6:
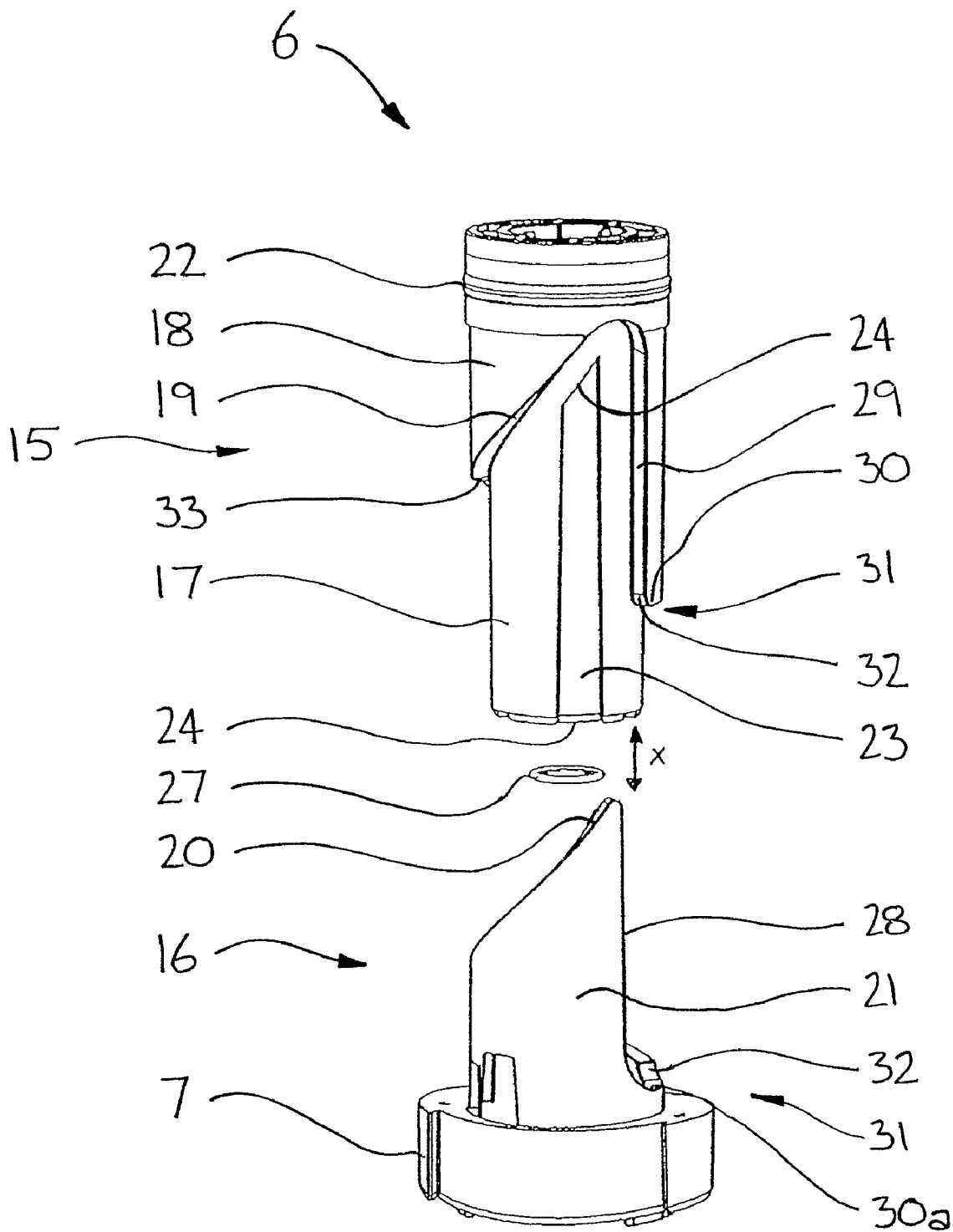
FIG. 6 is an exploded perspective view of the two-part piston.

It will be noted that the piston 6 comprises two separate parts, a body portion 15 and a handle portion 16 which are rigidly and immovably joined to each other once assembled. These two parts are shown more clearly in FIG. 6 from which it can be seen that the two parts join to each other along a line formed by the cam groove 9.

The body portion 15 comprises a stem 17 which is received and locates within the handle portion 16 and, a shoulder portion 18 which has a greater diameter than the stem 17 and a part helically shaped lower edge face 19 at the interface between the shoulder portion 18 and the stem 17 which corresponds in shape to a helically shaped upper end face 20 of a wall 21 upstanding from the handle 7 of the handle portion 16. A piston sealing member 22, such as a rubber O-ring seal, is mounted in a recess adjacent to the upper end of the shoulder portion 18 which slideably engages with the inner wall of the cylinder 5 to prevent escape of air and therefore loss of pressure through the gap between the cylinder 5 and the walls of the piston 6. The stem 17 includes a longitudinal recess 23 to receive a lug (not shown) protruding radially inwardly from the upstanding wall 21 of the handle portion 16 when the body and handle portions 15,16 are brought together (in the direction of arrow "X" in FIG. 6) so that the body portion 15 and the handle portion 16 can be connected together in only one orientation in which the helically shaped lower edge face 19 of the shoulder portion 18 and the helically shaped upper end face 20 of the wall 21 of the handle portion 16 together form the cam groove 9 around the circumference of the assembled piston 6. To ensure that the helically shaped lower edge face 19 and the helically shaped upper end face 20 are kept spaced from each other by a distance sufficient to allow the pin 7 to slide freely along the cam groove 8 therebetween, the stem 17 of the body portion 16 terminates with a base 24 against which a surface (not shown) on the handle portion 16 locates to prevent further insertion of the stem 17 into the handle portion 16 and so leave a space between the lower edge face 19 and upper end face 20 which is wide enough for the drive pin 7 to slide freely along as the piston 6 rotates.

Preferably, the stem 17 is held within the handle portion 16 by two screws. However, it will be appreciated that there is generally no need to separate the two components once they have been joined following manufacture and so some other means of fastening may alternatively be employed for example a weld or a snap fit.

The handle 7 may be a separate component that is attached to the remainder of the handle portion 16 using screws (see FIG. 5). A pump air inlet filter 26 is mounted between the handle portion 16 and the handle 7 to prevent the ingress of dirt into the chamber 5a that might otherwise block the valve assembly 12 or be inhaled by the user. The piston 6 also includes a non-return valve 27 to allow for the passage of air into the chamber 5a and piston 6 when the piston 6 is withdrawn from the cylinder 5 but seals to prevent escape of the air from the chamber 5a when the piston 6 is screwed back into the cylinder 5. The valve may be in the form of a diaphragm or a mushroom type valve.

As mentioned above, the inhaler 1 includes a mechanism to prevent movement of the piston 6 in the opposite direction. This makes it impossible for the user to unscrew the piston 6 from the cylinder 5 from its home position, as shown in FIG. 2, to its extended position, as illustrated in FIG. 3, as they would have to be able to turn it in the opposite direction to the direction the piston 6 is turned to screw it into the cylinder 5. Therefore, the piston 6 is constructed so that the user can slide the piston 6 directly out of the cylinder 5 by pulling it longitudinally in its axial direction without having to apply any rotational torque to the piston 5. This is achieved by providing the cam groove 9 with a straight section that extends longitudinally along the piston 6 and joins either end of the helical parts 9a together. The straight section is defined by a side edge 28 of the wall of the handle portion 16 and a corresponding side edge wall 29 of the shoulder portion 18 of the body 15 which are spaced from each other when the piston 6 is assembled, by a distance that allows the drive pin 7 to pass freely therealong when it passes out of the helical portion 9a of the cam groove 9 (see FIG. 6). The path defined by this straight section of the cam groove 9 enables the piston 6 to be withdrawn directly from the cylinder 5 without screwing it out, as the drive pin 8 travels along the path formed by the straight section.

As each end of the helical part 9a of the cam groove 9 is joined by the straight section, the cam groove 9 forms a complete loop or circuit along which the drive pin 8 travels as the piston 6 is manipulated by pulling or screwing it via the handle 7, as necessary. In a preferred arrangement, the circuit that the drive pin 8 travels is completed when the piston 6 has been rotated through 360 degrees such that it returns to its initial position after being rotated through this angle.

It will be appreciated that a particular advantage of the construction described above is that the piston 6 cannot be screwed back into the cylinder 5 to compress a charge of air until it has been pulled out of the cylinder 5 to its fullest extent possible. This is because the drive pin 8 can only move into the helical part 9a of the cam groove 9 after the piston 6 has been withdrawn to its fully extended position, as shown in FIG. 3. This has the advantage of preventing the user from attempting to compress a charge of air smaller than required for the inhaler 1 to function properly to aerosolise and entrain the full dose of the medicament stored in a blister.

The cam groove 9 may include a number of additional features to make the piston easier to manipulate. For example, there may be a region 31 intermediate the helical section 9a and the straight section of the cam groove 9 defined by the top of the side edge 30 of the shoulder portion 19 of the body 15 and the bottom 30a of the wall 21 of the handle portion 16. This region 31 is identified by having a pitch angle of substantially zero degrees relative to a plane perpendicular to the axis of the piston 6. When the piston 6 is in its home position, the pin 8 sits in the region 31 and prevents the piston 6 from being withdrawn from the cylinder 5 by applying an axial force thereto until the piston 6 has first been rotated through a small angle so that the pin 8 passes out of the region 31 into the straight section.

Once the piston 6 has been initially rotated so that the drive pin 8 is no longer sitting in the region 31 and lies in the straight section of the cam groove 9, no further rotation of the piston 6 is required and the piston 6 can be directly pulled from the cylinder 5 so that the drive pin 8 travels along the straight section of the cam groove 9.

It will also be appreciated that as the handle 7 has an oval shape in plan view, the user can visually see what position the piston 6 is in relative to the housing 2 before they turn it.

Similarly, a break in the helical part 9a of the cam groove 9 by introducing at least one "step" or rest point 33, possibly at a midpoint in the stroke of the piston 6 between the extended and home positions provides a point at which the user can let go of the piston 6 and re-orientate their hand to a more comfortable orientation to enable them to complete the rotation of the piston 6 back into the cylinder 5. The step 33 can be defined by a portion of the cam track 9 where the pitch angle of the track 9 is substantially zero degrees relative to a plane perpendicular to the axis of the pump cylinder 5, similar to the region 31 described above. A mechanism is provided to prevent the user rotating the piston 6 in the opposite direction at the start section 31 and in the inhale position B. If the cam track 9 is provided with a step 33 to provide a rest point for the user, the compression can be referred to as a two-stage compression stroke.

Figure 7:
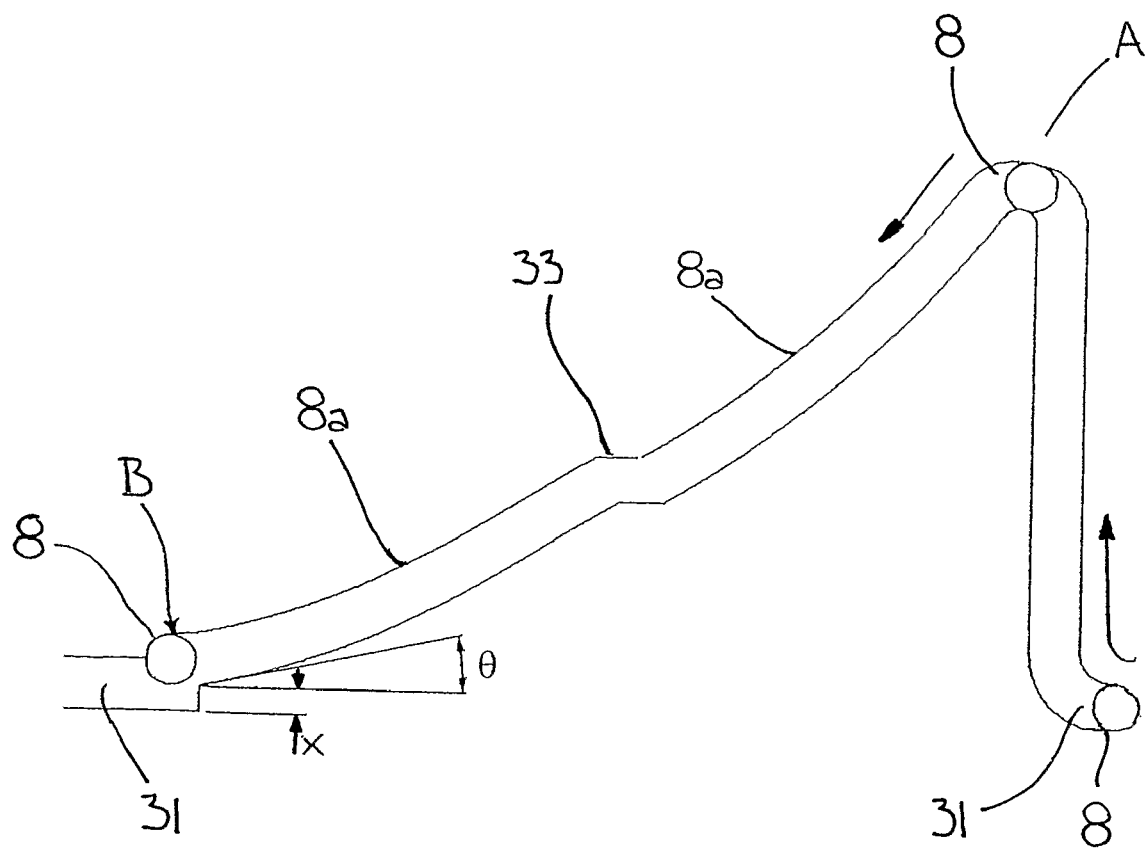
FIG. 7 is a diagram to illustrate the path that the pin may travel along the groove formed between the two parts of the piston when they are assembled.

A development of the cam groove 9 incorporating the region 31 and a rest point 33 at approximately the mid-point of the stroke, which is followed by the pin 8 as the piston 6 moves between the extended and home position is shown diagrammatically in FIG. 7. Starting from the right-hand side as viewed on the drawing, the inhaler 1 is in the position shown in FIG. 2. The cam track 9 has a region 31 where its pitch angle is substantially zero degrees and in which the pin 8 sits when the piston 6 is in its home position. The piston 6 is first rotated through an initial small angle so that the drive pin 8 moves out of the region 31 and into the base of the straight section of the cam groove 8. From this position, the piston 6 can be pulled directly out of the cylinder 5 to a fully extended position, as shown in FIG. 3, and in which the pin is located at point "A", as shown in FIG. 7. To compress a charge of gas or air, the user now begins to rotate the piston 6 so that the drive pin 8 engages the helical part 9a of the cam groove 9 until the pin 8 reaches the step or rest point 33, which is a point intermediate the ends of the helical part 9a of the cam groove 9 where the pitch angle of the track 9 is substantially zero degrees. The user will be able to tell when this position has been reached due to a change in the feel of the piston 6 and its direction of movement as they manipulate it. At this point, the user may release and move their hand to a more comfortable position on the handle 7 before continuing to screw the piston 6 into the cylinder 5 until the pin 8 reaches the end of the helical part 9a of the cam groove 9 (point B in FIG. 7). At this point, the generation of the charge of gas is complete and the pump is fully primed. Preferably an audible click is produced at this point to indicate to the user that the pump has reached the primed position. In a preferred embodiment said click is provided by a cantilever 70 mounted on the cylinder 5 clicking into a recess 71 in the handle portion 16. Advantageously the cantilever also acts as a non-return ratchet to prevent rotation of the piston to withdraw the piston from the cylinder. At this point the user may inhale through the mouthpiece 4 to release the gas through a pierced blister located in the valve module 12.

Once inhalation of the dose is complete and the charge of compressed air is exhausted, the user pushes the piston 6 into the cylinder 5 so that the drive pin 8 drops back into the region 31 and rotates the handle through a small angle to return the drive pin to the home position once more ready for the cycle to be initiated again. Preferably an audible click is produced at this point to indicate to the user that the pump has reached the home position. In a preferred embodiment said click is provided by the previously mentioned cantilever 70 mounted on the cylinder 5 clicking into a second recess 71 in the handle portion 16. Advantageously the cantilever also acts as a non-return ratchet to prevent rotation of the piston back to the primed position. As can be seen in FIG. 7, the piston 6 travels through a distance indicated by "X" to move the pin 8 out of the end of the helical part 9a of the cam groove 9 where it lies when the pump is fully primed and the inhaler 1 is used, back into the home position after use and the chamber 5a has been depressurised. The length of the region 31 may also be such that the piston 6 must be rotated through a small angle after being pushed back into the cylinder 5 to reach the home position.

When the chamber 5a is pressurised the drive pin 8 is in position B and the pressure acts on the piston 6 so as to prevent the drive pin 8 from moving down into the region 31. This means that it is difficult to return the drive pin 8 to its home position because the force acting over the top of the piston 6 must be overcome before it will move. For instance, if the pressure in the chamber 5a is 1.5 bar gauge and the cylinder 5 has a diameter of 28 mm, the force required to move the piston 6 is 92N (Force=Pressure×Area). As this force is difficult for the user to apply, it prevents them from returning the piston 6 to the storage position before depressurisation of the chamber 5a has occurred.

It is desirable that the user releases a charge of compressed gas shortly after priming the inhaler 1. Leaving the inhaler 1 in a primed state for extended periods of time should be avoided because the pressure in the chamber 5a may reduce due to leakage and prolonged stress on the components of the device. As the piston 6 must be pushed further into the cylinder 5 after exhaustion of a charge of gas, the user can easily determine whether the inhaler 1 is primed with a charge of gas or has been depressurised. When the chamber 5a has been depressurised, it is relatively easy for the user to push the piston 6 back into the cylinder 5 through the distance "X". However, it is much more difficult to do so whilst the chamber 5a is still charged due to the pressure in the chamber 5a which acts over the piston 6. This mechanism therefore acts as a detent which is pressure activated.

It will be appreciated that the combination of a cam track 9 forming a complete loop and a non-return mechanism means that the priming process is a one-way cycle which simplifies use of the inhaler 1 as the user only ever has to turn the handle 7 in the same direction making it much easier to use.

In accordance with another embodiment of the invention, the inhaler 1 can be made even more intuitive and easier to use by providing an interlock mechanism that prevents a user from operating the device in an incorrect way such as, for example, by following an incorrect sequence of operation. To achieve this, the housing 2 of the inhaler 1 may be provided with an elongate slide member 34 thereon incorporating a thumb plate 35 for manipulation by the user. This has the additional advantage of being external to the device and so the position of the slide member 34 is fully visible to the user. A series of drawings of an inhaler 1 incorporating a slide member 34 according to invention and showing the series of steps to be performed by the user during operation of the device is shown in FIGS. 8A to 8E and will now be described in more detail.

Figure 8A:
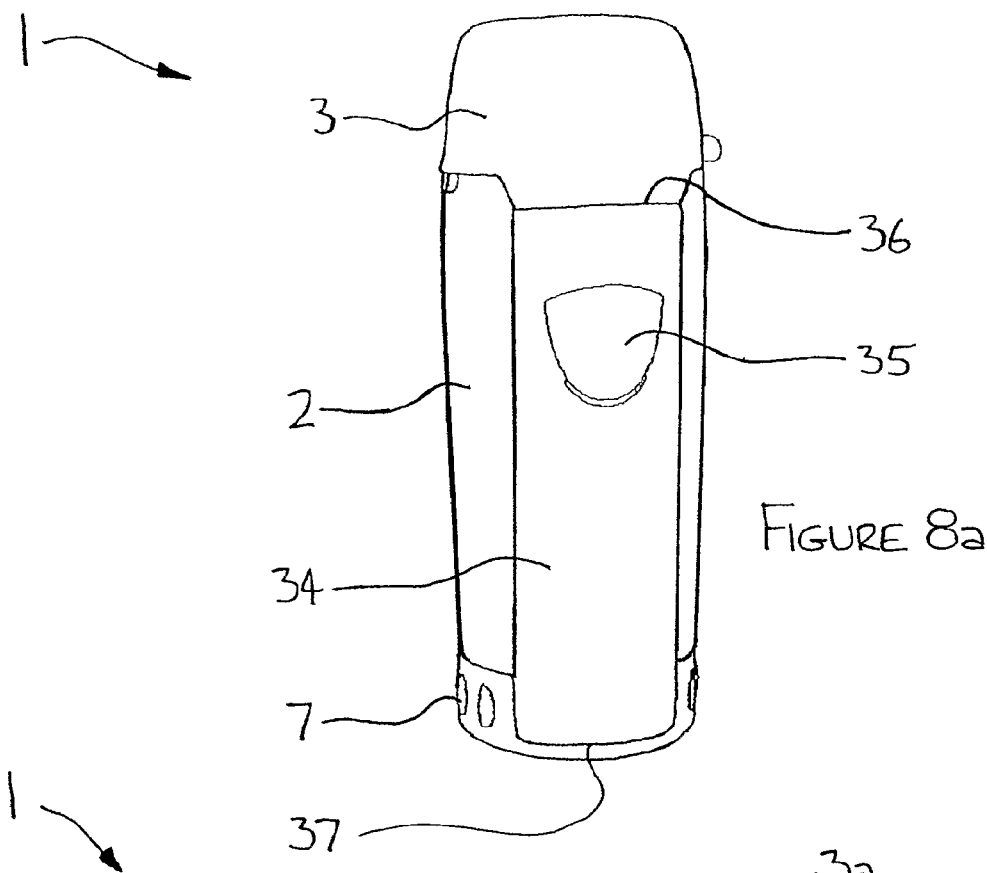
FIG. 8A to 8G is a series of drawings of an inhaler incorporating an interlock mechanism and showing the steps involved in its operation.

The inhaler 1 shown in FIG. 8A is shown in its storage mode when it is not in use. This is the state in which the inhaler 1 should be in when a user is carrying it and it is not in use. As can be seen in the drawing, the cap 3 is closed over the mouthpiece 4 to protect it and the piston 6 is in its home position, as also shown in the cross-sectional view of the inhaler 1 shown in FIG. 2.

The slide member 34 extends substantially the entire length of the housing 2 and its uppermost end 36 is in contact with the edge 3a of the cap 3. The lower end 37 of the slide member 34 extends beyond the bottom of the housing 2 and is received in a recess or depression 38 formed in the side of the handle 7. In this position, the slide member 34 prevents any rotation of the handle 7 and so of the piston 6, which is required to move the pin 8 out of the region 31 and into the straight section of the cam track 9a, because the handle 7 is interlocked with the slide member 34.

Figure 8B:
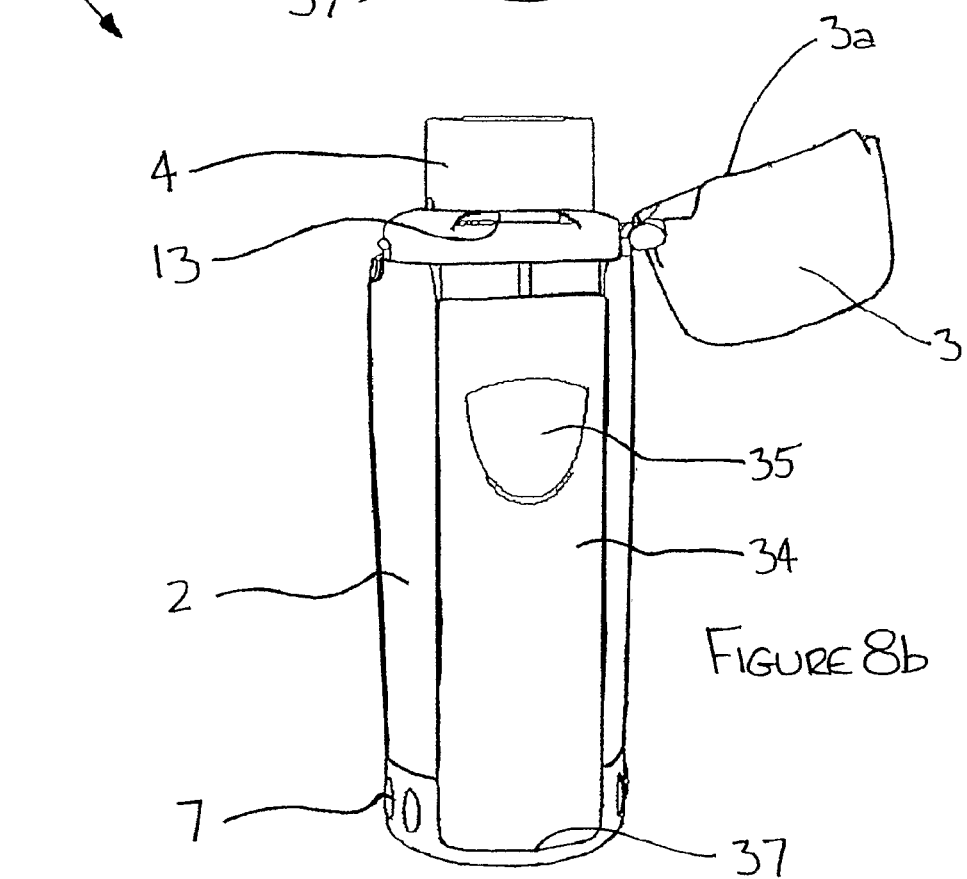

The first step in the sequence of operation of the inhaler 1 is to open the cap 3, as shown in FIG. 8B. The slide member 34 cannot be slid upward until the cap 3 has been opened and therefore the user is encouraged to open the cap 3 first to enable them to subsequently move the slide member 34. Once the cap 3 is open, the blister slot 13 is revealed prompting the user to insert a blister containing a measured dose of medicament to be inhaled into the valve module 12 through the slot 13. The slot 13 is formed in the sidewall of the mouthpiece 4 adjacent to the region that is placed in the mouth. This is an ideal location for the blister slot 13 as it is protected from the ingress of dust and moisture by the cap 3 when it is closed, thereby removing the requirement for additional protection for the slot 13, such as a shutter.

Figure 8C:
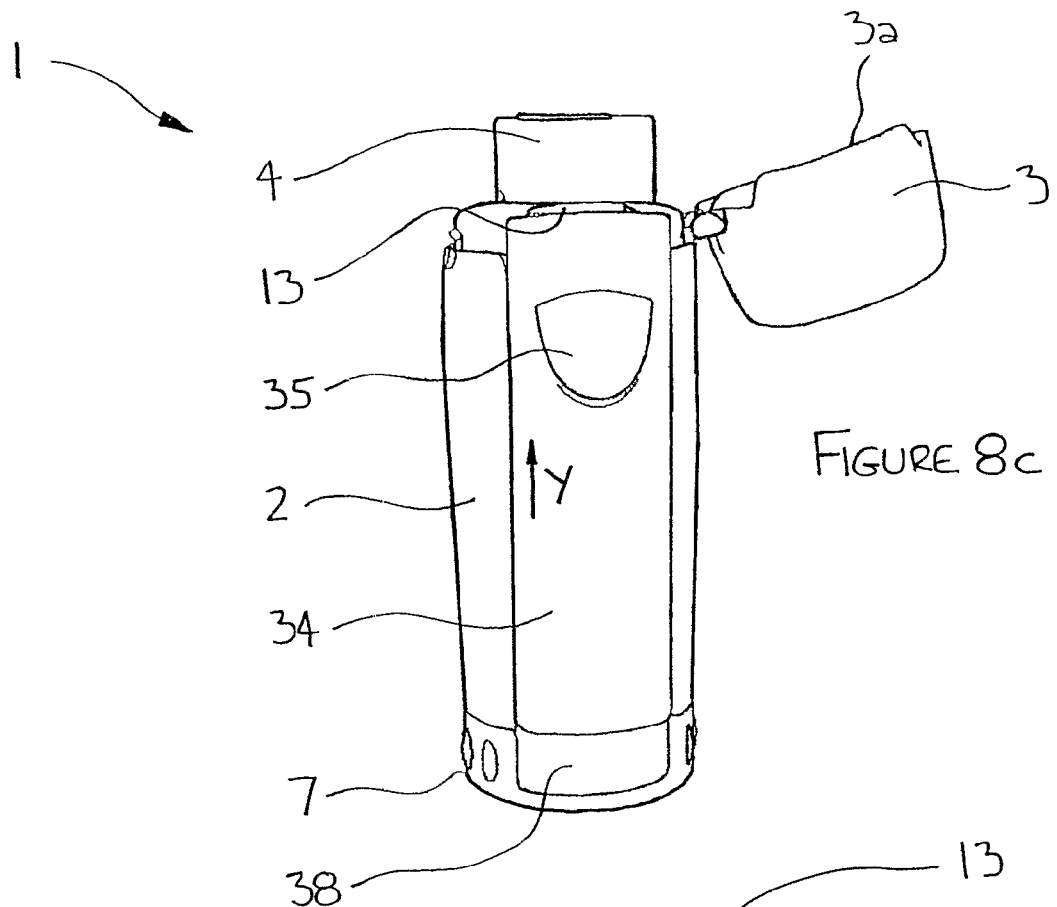

Once the blister is in place within the slot 13, the slide member 34 can be slid in the direction of arrow "Y" towards the mouthpiece 4 and into a position shown in FIG. 8C, this movement of the slide member 34 no longer being prevented by the now open cap 3. As the slide member 34 moves upward, the handle 7 is disengaged so that it can now be rotated through a small angle to enable it to be subsequently pulled out of the cylinder 5 into its extended position. At the same time, the slide member 34 causes the blister to be clamped and pierced and so prevents a user from removing the blister until the slide member 34 has been moved back into its original position, as shown in FIG. 8A.

Figure 8D:
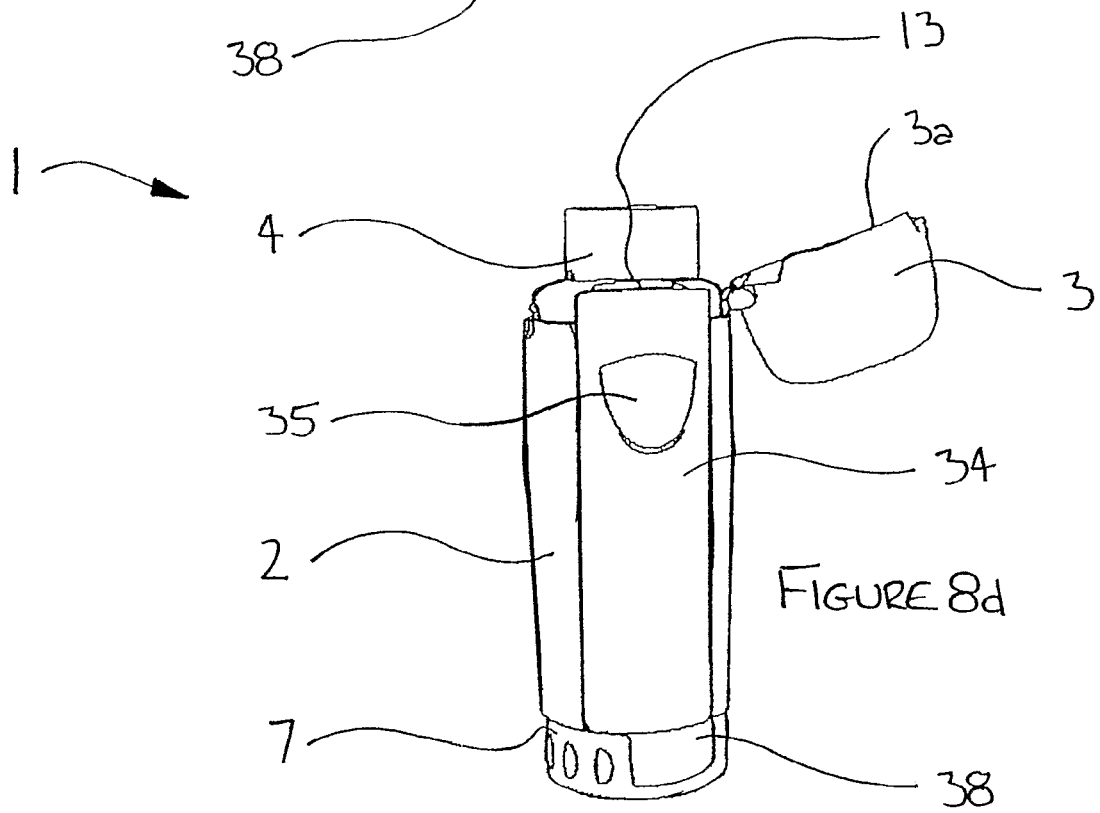
Figure 8E:
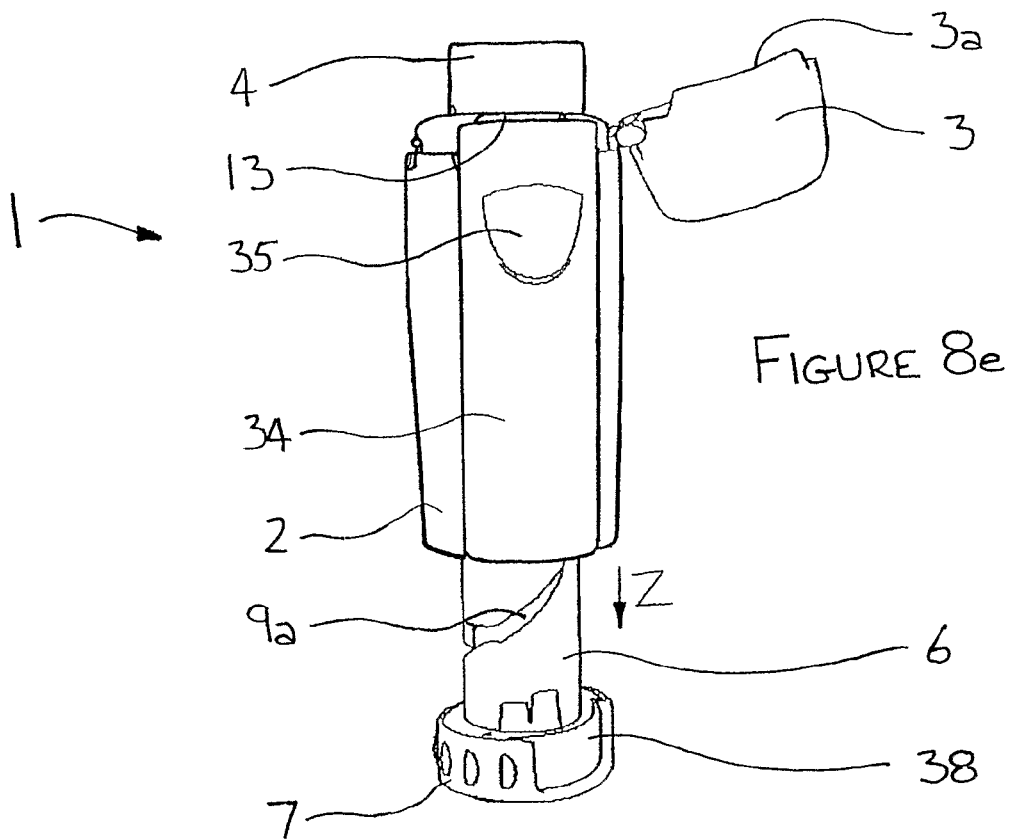
Figure 8F:
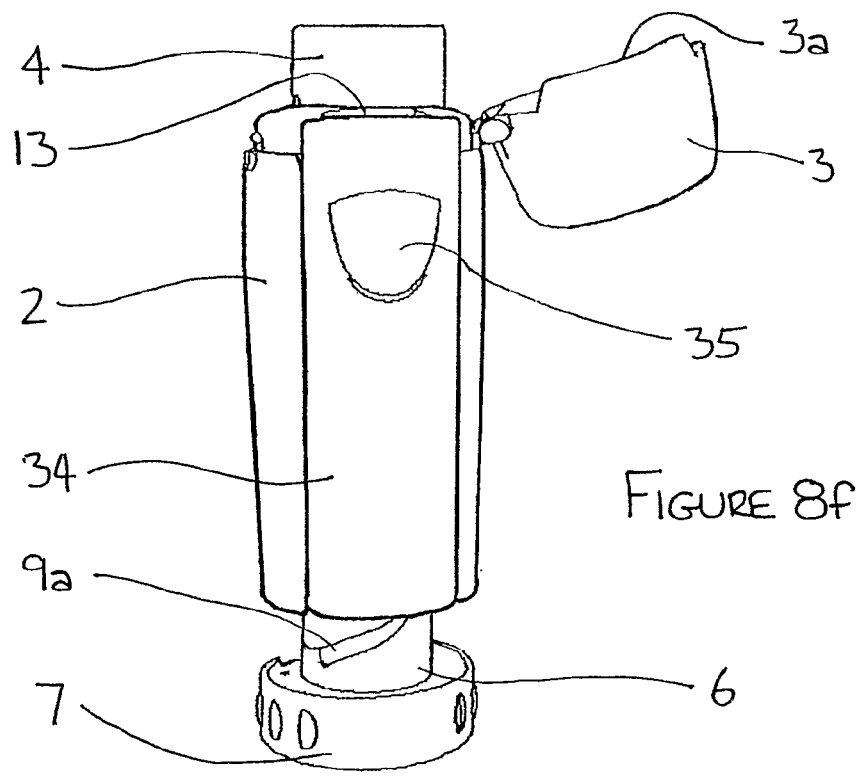

In FIG. 8D, the piston 6 has been rotated through a small angle relative to the housing 2 to free the drive pin 8 from the region 31 of the helical part 9a of the cam groove 9 so that it now sits at the base of the straight section. The piston 6 can now be pulled directly out of the cylinder 5 by pulling it in the direction shown by arrow "Z" in FIG. 8E, the drive pin 8 sliding along the straight section of the cam groove 9 as the piston 6 is pulled from the cylinder 5. Once the piston 6 has reached its fullest extent, and only when it has reached its fullest extent, the piston 6 can be rotated by the user to drive it back into the cylinder 5, as shown in FIG. 8F, to compress a charge of gas therein. The piston 6 cannot be screwed in at all until it has been pulled out to its fullest extent because the drive pin 8 in the cam track 9 has to follow the track 9.

Figure 8G:
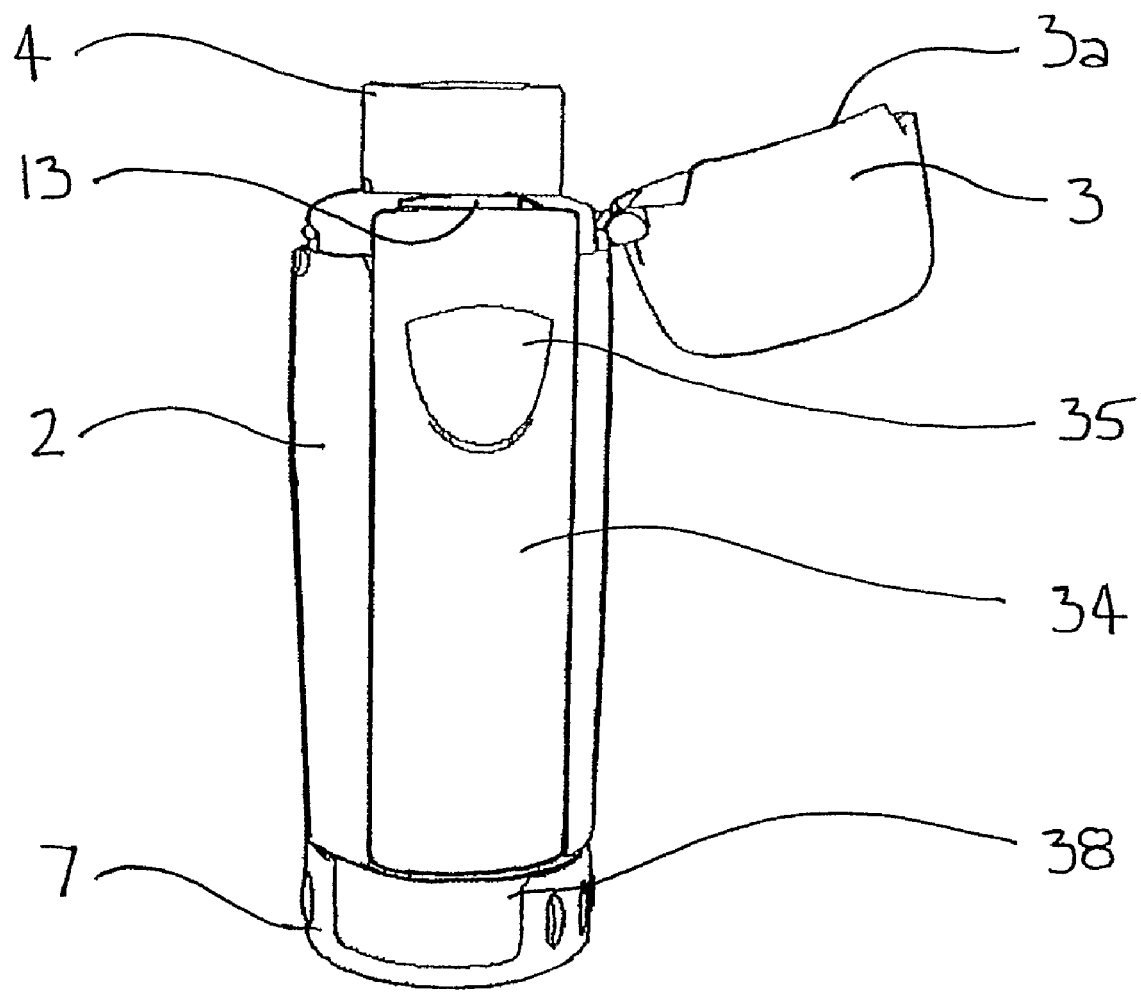

Once the piston 6 has been twisted back in so that the pin 8 has traveled along the full length of the helical part 9a of the cam groove 9, as shown in FIG. 8G, the user then inhales through the mouthpiece 4 to release the charge of gas through the blister and into the patient's airway via the mouthpiece 4. The piston 6 can then be pushed to the housing 2 through a final small distance ("X" in FIG. 7) so that the pin 8 drops back into the region 31. Once it has been pushed in, rotation of the piston 6 through a small angle will return it to its home position, as shown in FIG. 8A, once again.

The manufacture of a piston 6 with a threaded form by injection moulding is a difficult process made even more complicated if the thread has a variable or non-uniform pitch. Constant pitch threads can be formed on the inside of a cylindrical injection moulded component using a core on the moulding tool that unscrews to eject the part. However, this is clearly not possible with a thread having a variable pitch. Therefore, in an arrangement suited to high volume manufacturing using injection moulding, the variable pitch cam groove 9 is carried on the piston 6 rather than on the outer cylinder 5 in which the piston moves.

Even with the aforementioned arrangement, it will be appreciated that the thread form requires a complex injection moulding tool with a number of "side actions" in order to form the edges of the thread around the outside of the piston 6. This makes the tool very complicated and is likely to shorten its life. A further disadvantage of this arrangement is that because some parts of the tool forming the cam groove 9 do not move radially to the axis of the piston, the walls of the cam groove 8 cannot be kept normal to the wall of the piston 6 at all points. This means that the load bearing capability of the cam groove 9 is reduced.

Furthermore, in high volume manufacturing it is desirable to form multiple copies of each component in the same tool. This is known as multiple cavity tooling. However, because of its complexity, the tool required for the piston 6 would be limited to fewer cavities than a simpler tool and this would add to the cost of manufacturing the part.

It will therefore be appreciated that the formation of the piston 6 from two parts that are joined along an edge, which defines the form of the cam groove 9, allows each component to be moulded in a straightforward manner using a much simpler mould tool. A further advantage is that the walls of the cam groove 8 can be kept normal along their whole length.

As previously mentioned, it is desirable to provide an inhaler that cannot be misused. One form of misuse is the deliberate or inadvertent release of only a partial charge of compressed air. This could occur, for example, if the user operated the inhaler 1 when the piston 6 was at the rest point 33 intermediate the ends of the helical part 9a of the cam groove 9. This is obviously undesirable as the dose will not be entrained, aerosolised or delivered to the patient correctly. Furthermore, if the user released a partial charge of compressed air, they might then go on to complete the priming cycle by driving the piston 6 back into the cylinder without withdrawing it first. The inhaler 1 would then appear to be fully charged when in reality, it would only be partially charged.

To prevent release of a charge before compression is complete, an embodiment of the inhaler 1 of the present invention includes an interlock so that the inhaler 1 cannot be actuated until the compression stroke has been completed.

As mentioned above, the inhaler 1 of the present invention comprises a valve module 12 which closes the upper end of the cylinder 5 and has a path therethrough for the passage of compressed air from the chamber 5a through a dose of medicament contained in a blister mounted in the valve module 12 adjacent to a piercing element (not shown) and into the mouthpiece 4 from which it is inhaled into the patient's airway. The valve module 12 comprises a dual mode valve for controlling the release of gas from the chamber 5a in which a main diaphragm 40, which prevents the release of a charge of compressed air from the chamber 5a, is opened when the pressure generated in a primary or pilot reservoir 41 on one side of the diaphragm 40, opposite to the side acted on by the pressure in the chamber 5a and sufficient to hold the diaphragm 40 closed against a valve seat 42 and so prevent release of the charge from the chamber 5a, is reduced to a level at which the pressure generated in the chamber 5a overcomes the pressure generated in the pilot reservoir 41 and so causes the diaphragm 40 to move away from the valve seat 42 thereby opening the valve and releasing the charge of compressed air from the chamber 5a. This breath actuated valve arrangement is described in detail in the Applicant's co-pending application no. 0321610.8 filed on 15 Sep. 2003.

In order to ensure that the main diaphragm 40 does not open during charging, it is important to ensure that the pilot reservoir 41 is pressurised prior to pressurisation of the chamber 5a. In a preferred embodiment of the present invention, this is achieved by providing the valve member 12 with two closable ports 43,44, a pilot reservoir port 43 to control flow of gas from the chamber 5a to the pilot reservoir 41, and a main diaphragm port 44 to control the flow of gas from the chamber 5a to a region in which it acts on the side of the diaphragm 40 facing the chamber 5a.

Figure 9:
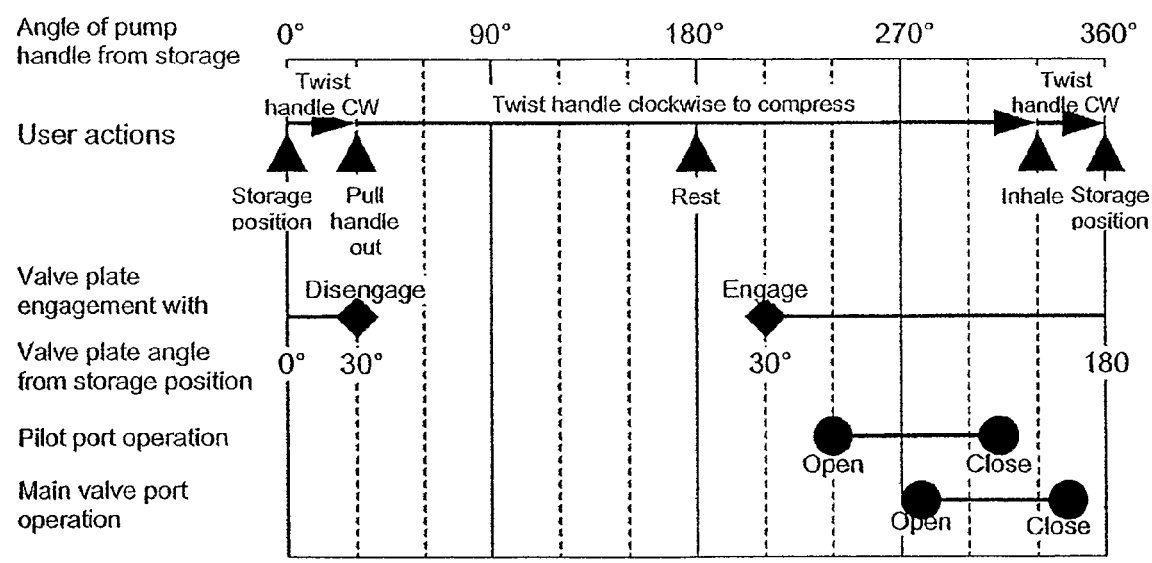
FIG. 9 is a diagram to show the sequence of opening of ports in the valve module between the chamber and the main valve diaphragm and the chamber and the pilot reservoir.

In a preferred arrangement, the timing of the opening and closing of the aforementioned ports 43,44 is controlled in dependence on the position of the piston 6 within the cylinder 5. A particularly advantageous timing sequence is illustrated in FIG. 9. According to this sequence, the pilot reservoir port 43 is opened prior to opening the main diaphragm port 44 and the pilot reservoir port 43 closes before the main valve diaphragm port 44 closes. It will also be appreciated from FIG. 9 that neither of the ports 43,44 open until late in the compression cycle i.e. when the air in the chamber is virtually fully compressed and ready to be released. The main diaphragm port 44 remains open during firing and closes as the piston 6 is returned to its storage position after firing.

It will also be appreciated that by ensuring that the pilot reservoir port 43 is opened prior to opening of the main diaphragm port 44, the pilot reservoir 41 is always charged prior to pressure acting on the other side of the diaphragm 40 from the chamber 5a. This means that there is no need for a mechanical device such as a spring, to act on the diaphragm 40 to keep it closed before the pilot reservoir 41 is charged.

The aforementioned configuration ensures that the charge of gas cannot be released until a user has substantially fully primed the chamber 5a with a charge of compressed air. If they attempt to do so, any initial charge that has built up in the chamber 5a will not be released because neither the main diaphragm port 43 or the pilot reservoir port 44 are open until the chamber 5a has been fully primed or almost fully primed. Therefore, the risk of delivering an incorrect dose is avoided or reduced.

It will also be appreciated from FIG. 9, that the pilot reservoir port 43 is closed before priming is complete. If the pilot reservoir port 43 were not closed, firing of the device would result in part of the charge leaking through the pilot chamber dump port (not shown) which vents the pilot chamber to atmosphere on firing and being lost.

The opening and closing of the main diaphragm and pilot reservoir ports 43,44 is controlled, according to a preferred embodiment of the invention, by a rotary valve plate 45 actuated as the piston 6 rotates into the cylinder 5 during priming of the pump. The actuation mechanism will now be described with reference to FIGS. 10 to 13.

From the side sectional views of FIGS. 12 and 13, it can be seen that the rotary valve plate 45 of the valve module 12 has a stem 46 that protrudes into the chamber 5a. A pair of vanes 47 extend radially from the stem 46 into the chamber 5a. The piston 6 (not shown) is provided with axial grooves which co-operate with the vanes 47 on the stem 46 during rotation of the piston 6 into the cylinder 5 so that as the piston 6 is twisted by turning the handle 7 to compress a charge of gas, the grooves pick up on the vanes 47 after which the rotary valve plate 45 rotates together with the piston 6 during further movement of the piston 6 into the chamber 5a. The axial grooves have a lead-in portion (not shown) to facilitate engagement with the vanes. The depth of extension of the vanes 47 into the chamber 5a is such that the valve plate 45 is only engaged with the piston 6 over approximately the last 180 degrees of rotation of the piston 6. As the piston 6 moves approximately 360 degrees in a complete compression cycle, it will be appreciated that the rotary valve plate 45 rotates through an angle of about 180 degrees. When the piston 6 is withdrawn from the cylinder 5, the grooves slide free from the vanes 47 and disengage the valve plate 45 from the piston 6.

The rotary valve plate 45 has a first aperture 48 therein which is positioned to align in one position of the rotary valve plate 45, with the main diaphragm port 44 that is in communication with one side of the main valve diaphragm 40. When the rotary plate 45 rotates in response to engagement thereof by the piston 6, the first aperture 48 moves into alignment with the main diaphragm valve port 44 thereby communicating the pressure generated in the chamber 5a with one side of the diaphragm 40.

Similarly, the rotary valve plate 45 includes a second aperture 49 therein which is positioned to align, in one position of the rotary valve plate 45, with the pilot reservoir port 43 which is in communication with the pilot reservoir 41 and so the other side of the main valve diaphragm 40. The second aperture 49 and the pilot reservoir port 43 can be brought into alignment with each other in response to rotation of the rotary valve member 45 to communicate the chamber 5a with the pilot reservoir 41 via the aperture 49 in the valve plate 45 and the pilot reservoir port 43.

To ensure that the pilot reservoir port 43 opens prior to opening of the main valve diaphragm port 44, and the pilot reservoir port 43 closes before the main valve diaphragm port 44 closes, the first and second apertures 48,49 in the rotary valve plate 45 are located relative to each other so that the second aperture 49 moves into alignment with the pilot reservoir port 43 before the first aperture 48 moves into alignment with the main diaphragm port 44 and so that the second aperture 49 moves out of alignment with the pilot reservoir port 43 before the first aperture 48 moves out of alignment with the main diaphragm port 44, as the rotary valve plate 45 rotates. It will be appreciated that the first and second apertures 48,49 in the rotary valve plate 45 are arcuate in shape so that there is an overlap in which both the pilot reservoir port 43 and the main diaphragm valve port 44 are aligned with the second and first apertures 48,49 in the rotary valve plate 45 respectively.

To prevent leakage of compressed air through the first and/or second apertures 48,49, a sealing member 50, such as a rubber O-ring seal, is located on the valve module 12 at the interface between the pilot reservoir port 43 and the rotary valve plate 45 and between the main diaphragm port 44 and the rotary valve plate 45. To compress the sealing members 50 and seal the ports 43,44, the rotary valve plate 45 is bolted to the valve body 12 via a spring washer 51.

As shown in the drawings, the rotary valve plate 45 is provided with two sets of apertures 48,49. This means that a set of ports 48,49 is always in the correct position for the next cycle of operation after the valve plate 45 has been rotated by 180 degrees during a previous cycle of operation.

Many modifications and variations of the invention falling within the terms of the appended claims will be apparent to those skilled in the art. For example, although the embodiments described above refer to an inhaler in which the piston slideably moves within a cylinder, it would also be possible to envisage an embodiment in which the piston itself is fixed and the cylinder slides over the piston. Therefore, the foregoing description should be regarded as a description of the preferred embodiments only.

The invention claimed is:

1. An inhaler for the delivery of a dose of a powdered medicament for inhalation by a user comprising a housing containing a cylinder and a piston together defining a chamber, the piston and the cylinder being slideable relative to each other during a compression stroke in response to the application of a load thereto by the user to generate a charge of compressed air in the chamber for entraining the dose when the charge is released, the inhaler including means for increasing the mechanical advantage during the compression stroke so that the effort applied by the user remains substantially constant throughout the compression stroke irrespective of the increase in pressure in the chamber;

wherein the effort applied by the user during the compression stroke is a torque operable to rotate the piston and said means is configured so that the linear distance traveled by the piston per angle through which it rotates during the compression stroke reduces to increase the mechanical advantage.

2. An inhaler according to claim 1, wherein the means comprises a cam track and a pin located in the cam track so as to slide freely therein during rotation of the piston.

3. An inhaler according to claim 2, wherein the cam track is formed in the piston and the pin is mounted so as to extend radially into cylinder and locate in the cam track.

4. An inhaler according to claim 2, wherein at least a portion of the cam track follows a helical path that extends along the axis around the outside of the piston.

5. An inhaler according to claim 4, wherein ends of the helical portion of the cam track are joined by a second straight portion of cam track extending parallel to the axis of the cylinder so that the cam track forms a complete circuit for the pin during movement of the piston into and out of the cylinder.

6. An inhaler according to claim 5, wherein the helical portion of the cam track extends substantially 360 degrees around the piston.

7. An inhaler according to claim 5, wherein the cam track includes a region between the helical portion and a straight portion having a pitch that is substantially zero degrees relative to a plane perpendicular to the axis of the cylinder.

8. An inhaler according to claim 7, wherein the pin locates in said region when the piston is in a home position in which the piston is fully retracted into the cylinder.

9. An inhaler according to claim 8, wherein the cam track includes a detent therein intermediate the ends of said region configured so that the pin and the detent co-operate with each other during initial rotation of the piston so that additional torque must be applied to the piston by the user to force the pin past the detent and so rotate the piston out of its home position.

10. An inhaler according to claim 7, wherein the helical portion of the cam track includes another region intermediate its ends having a pitch that is substantially zero degrees relative to a plane perpendicular to the axis of the cylinder.

11. An inhaler according to claim 8, including an interlock mechanism to prevent rotation of the piston out of said home position prior to movement of the interlock mechanism.

12. An inhaler according to claim 11, wherein the interlock mechanism comprises a slide member on the housing movable into and out of engagement with the piston when the piston is in its home position.

13. An inhaler according to claim 10, including a mouthpiece and a cap pivotable between an open position for inhalation through the mouthpiece and a closed position in which the mouthpiece is covered by the cap, wherein movement of the slider is prevented when the cap is in the closed position.

14. An inhaler according to claim 2 wherein a helical portion of the cam track has a pitch angle that varies along the length of the piston so that the linear distance traveled by the piston reduces relative to the angle through which it rotates during the compression stroke to increase the mechanical advantage.

15. An inhaler according to claim 1 wherein the piston comprises a body portion and a handle portion, a cam track being formed at an interface between the body portion and the handle portion.

16. An inhaler according to claim 15, wherein the body portion comprises a stem part and a head part of larger diameter than the stem part, a part helically shaped shoulder being formed at the interface between the head part and the stem part.

17. An inhaler according to claim 16, wherein the handle portion comprises a cylindrical body to receive the stem part of the body portion, an end face of the handle portion in which the stem part is received being part helical in shape to correspond to the part helically shaped shoulder of the body portion.

18. An inhaler according to claim 15, wherein the body portion and the handle portion include co-operating means that engage to fit the stem part in the cylindrical body in only one orientation.

19. An inhaler according to claim 18, wherein the co-operating means comprises a radially inwardly depending lug on the handle portion that locates in a rebate formed in the surface of the stem part of the body portion.

20. An inhaler according to claim 19, wherein the base of the stem engages with a surface of the handle to prevent further insertion of the stem part into the handle portion, the opposing part helically shaped shoulder and part helically shaped end face being spaced from each other to form the sidewalls of the cam track.

21. An inhaler according to claim 1 further comprising a valve module including a valve body and a rotary valve plate rotatably mounted on the body, the piston and the rotary valve plate including co-operating means that engage as the piston is rotated into the cylinder so that the rotary valve plate rotates together with the piston relative to the valve body.

22. An inhaler according to claim 21, wherein the valve body includes a main diaphragm valve port and a pilot reservoir port, the rotary valve plate being configured to open and close said ports as the rotary valve plate rotates.

23. An inhaler according to claim 22, wherein the rotary valve plate has first and second apertures therein that align with the main diaphragm valve port and the pilot reservoir port respectively, as the rotary valve plate rotates, to open said ports.

24. An inhaler according to claim 23, wherein the apertures in the rotary valve plate are configured such that the pilot reservoir port is opened prior to opening of the main diaphragm port.

25. An inhaler according to claim 23, wherein the apertures in the rotary valve plate are configured such that the pilot reservoir port is closed prior to closing of the main diaphragm port.

26. An inhaler according to claim 22, wherein the charge of compressed gas is exhausted through the main diaphragm port when the charge is released.

27. An inhaler according to claim 21, wherein the rotary valve plate is configured to prevent the release of a charge of compressed gas from the chamber until the chamber is substantially fully primed.

28. An inhaler according to claim 21, wherein the co-operating means engage for approximately a last 180 degrees of rotation of the piston into the cylinder so that the rotary valve plate rotates relative to the valve module through 180 degrees. from the chamber until the chamber is substantially fully mimed.

29. An inhaler according to claim 28, wherein the rotary valve plate has a second set of first and second apertures provided therein.

* * * * *